United States Patent [19]

Adin et al.

[11] Patent Number: 4,459,351

[45] Date of Patent: Jul. 10, 1984

[54] PHOTOGRAPHIC ELEMENT AND PROCESS EMPLOYED COMBINATION OF SURFACE AND INTERNAL LATENT IMAGE SILVER HALIDE

[75] Inventors: Anthony Adin; Henry W. Altland, both of Rochester, N.Y.

[73] Assignee: Eastman Kodak Company, Rochester, N.Y.

[21] Appl. No.: 507,181

[22] Filed: Jun. 22, 1983

[51] Int. Cl.³ .......................... G03C 5/54; G03C 1/46; G03C 5/38
[52] U.S. Cl. .................................. 430/445; 430/202; 430/502; 430/506; 430/509; 430/564; 430/566; 430/596; 430/955; 430/957; 430/223
[58] Field of Search ............... 430/202, 219, 223, 445, 430/502, 506, 596, 611, 955, 957, 564, 509, 566

[56] References Cited

U.S. PATENT DOCUMENTS

| | | | |
|---|---|---|---|
| 2,592,250 | 4/1952 | Davey et al. | 95/7 |
| 2,996,382 | 8/1961 | Luckey et al. | 96/68 |
| 3,178,282 | 4/1965 | Luckey et al. | 96/68 |
| 3,206,313 | 9/1965 | Porter et al. | 96/108 |
| 3,379,529 | 4/1968 | Porter et al. | 96/36 |
| 3,639,417 | 2/1972 | Porter et al. | 260/308 D |
| 3,695,881 | 10/1972 | Luckey | 96/29 |
| 3,740,226 | 6/1973 | Dappen et al. | 430/596 |
| 4,105,452 | 8/1978 | Shiba et al. | 96/74 |
| 4,108,663 | 8/1978 | Tanaka et al. | 430/957 |
| 4,335,199 | 6/1982 | Mickewich et al. | 430/434 |
| 4,351,896 | 9/1982 | Altland et al. | 430/354 |

OTHER PUBLICATIONS

*Research Disclosure*, Dec. 1978, Item No. 17643.

*Primary Examiner*—Richard L. Schilling
*Attorney, Agent, or Firm*—Richard E. Knapp

[57] ABSTRACT

A redox release compound that is capable upon oxidation of releasing a silver ion complexing heterocyclic thio moiety enables reduction of the concentration of silver required in a photographic silver halide material comprising a combination of (i) photographic silver halide capable of forming a surface latent image, and (ii) a photographic silver halide capable of forming an internal latent image. The silver halide capable of forming an internal latent image preferably has lower photosensitivity than the silver halide capable of forming a surface latent image. The redox release compound preferably comprises a silver ion complexing 1,2,4-triazolium-3-thio moiety. An image is developed in such an exposed photographic silver halide element by means of a surface type silver halide developer.

17 Claims, No Drawings

PHOTOGRAPHIC ELEMENT AND PROCESS EMPLOYED COMBINATION OF SURFACE AND INTERNAL LATENT IMAGE SILVER HALIDE

BACKGROUND OF THE INVENTION

1. Field of the Invention

This invention relates to a photographic silver halide material comprising a redox release compound that is capable, upon oxidation, of releasing a silver ion complexing heterocyclic thio moiety which enables reduction of the concentration of silver required in the photographic material. It also relates to such redox release compounds which preferably comprise a silver ion complexing 1,2,4-triazolium-3-thio moiety.

2. Description of the State of the Art

Photographic silver halide materials comprising combinations of surface sensitive photographic silver halide and fogged internally sensitive photographic silver halide are known in the photographic art. Examples of such photographic silver halide materials are described in, for instance, U.S. Pat. No. 4,335,199; U.S. Pat. No. 2,996,382 and U.S. Pat. No. 3,178,282. A problem encountered in such materials has been the need to provide a significant concentration of iodide, such as that released from silver iodide to enable development of the fogged internally sensitive photographic silver halide in such materials. A problem encountered in the photographic materials of U.S. Pat. No. 4,335,199 has been that the photosensitivity of the internally sensitive photographic silver halide must be equal to or greater than the photosensitivity of the surface sensitive photographic silver halide. This is difficult because this requires more total silver in the photographic silver halide material than otherwise might be required. It has been desirable to avoid the need for iodide, such as from silver iodide, and to enable a photographic silver halide material that reduces the concentration of total silver needed to provide a developed image in such photographic materials comprising mixed surface sensitive photographic silver halide and internally sensitive photographic silver halide. It has also been desirable to enable contrast enhancement in such photographic silver halide materials.

A need has also existed for new organic compounds that enable reduction of total silver concentration in a photographic silver halide material comprising a combination of a surface sensitive photographic silver halide and an internally sensitive photographic silver halide.

SUMMARY OF THE INVENTION

According to the invention, reduced concentrations of silver are required in a photographic material comprising photographic silver halide in reactive association with a redox release carrier compound containing a silver ion complexing heterocyclic thio moiety that is capable of being released upon oxidation of the redox release carrier compound. The photographic silver halide comprises a combination of (i) photographic silver halide capable of forming a surface image, and (ii) a photographic silver halide capable of forming an internal latent image.

The photographic silver halide capable of forming an internal latent image preferably has lower photosensitivity than the silver halide capable of forming a surface latent image. The silver ion complexing heterocyclic thio moiety is also capable of (a) being released as a function of development of the surface latent image silver halide, and (b) migrating to the internal latent image silver halide to uncover the internal latent image and rendering the internal latent image silver halide developable.

The imagewise development of the internal latent image in the internally sensitive silver halide enables enhancement of the silver image density developed in the surface sensitive photographic silver halide. This enables the total concentration of silver in the photographic material to be reduced without adversely affecting the final developed silver image and without the need for other imaging mechanisms and added imaging compounds, such as dyes. The photographic material according to the invention also enables processing without the need for special developers, such as special internal image developers.

The photographic material according to the invention preferably comprises a new redox release carrier compound containing a silver ion complexing 1,2,4-triazolium-3-thio moiety that is capable of being released upon oxidation of the redox release carrier. Preferred new redox release carrier compounds containing a silver ion complexing 1,2,4-triazolium-3-thio moiety are represented by the formula:

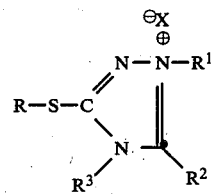

wherein:
R is redox release carrier moiety capable upon oxidation of releasing a silver ion complexing moiety, that is the 1,2,4-triazolium-3-thio moiety;

$R^1$, $R^2$ and $R^3$ are individually alkyl, preferably alkyl containing 1 to 25 carbon atoms, such as methyl, ethyl, propyl, butyl, decyl, eicosyl and pentacosyl; alkenyl, preferably alkenyl containing 2 to 25 carbon atoms, such as $-CH=CH_2$, $-CH=CH-CH_3$, $-CH=CH-CH=CH_2$ and $-CH=CH-CH=CH-CH_2CH_3$; aryl, preferably aryl containing 6 to 25 carbon atoms, such as phenyl and naphthyl; alkoxy, preferably alkoxy containing 1 to 25 carbon atoms, such as methoxy, ethoxy, decyloxy and pentacosyloxy; or

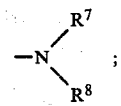

$R^7$ is hydrogen or alkyl, preferably alkyl containing 1 to 25 carbon atoms, such as methyl, ethyl, propyl, butyl, decyl, eicosyl and pentacosyl;

$R^8$ is hydrogen; alkyl, preferably alkyl containing 1 to 25 carbon atoms, such as methyl, ethyl, propyl, butyl, decyl, eicosyl and pentacosyl; or aryl, preferably aryl containing 6 to 25 carbon atoms, such as phenyl and naphthyl; and X is an anion, such as p-toluenesulfonate (PTS⊖); nitrate; trifluoroacetate; tetrafluoroborate (BF₄⊖); chloride; bromide; iodide; and sulfate.

Another preferred photographic material according to the invention comprises a redox release carrier compound containing a silver ion complexing 2-mercapto-5-substituted ureido-1,3,4-thiadiazole moiety that is capable of being released upon oxidation of the redox release carrier. Preferred redox release carrier compounds containing a silver ion complexing 2-mercapto-5-substituted ureido-1,3,4-thiadiazole moiety are represented by the formula:

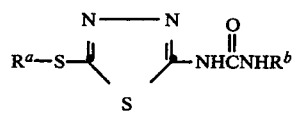

wherein:
- $R^a$ is a redox release carrier moiety capable upon oxidation of releasing a silver ion complexing moiety, that is the 2-mercapto-5-ureido-1,3,4-thiadiazole moiety;
- $R^b$ is a substituent which does not adversely affect the carrier moiety or the silver ion complexing activity of the 2-mercapto-5-ureido-1,3,4-thiadiazole moiety. $R^b$ is preferably alkyl, such as alkyl containing 1 to 25 carbon atoms, for example methyl, ethyl, propyl, butyl, pentyl and eicosyl; or aryl, such as aryl containing 6 to 12 carbon atoms, for example, phenyl or naphthyl. $R^a$ is preferably a phenolic redox release carrier moiety. The term phenolic herein includes both phenolic and naphtholic compounds.

The method of forming an image in an exposed photographic silver halide element according to the invention comprises developing the element by means of a surface type silver halide developer. Such a process enables imagewise development of both the surface sensitive photographic silver halide and the internally sensitive photographic silver halide.

A variety of silver ion complexing heterocyclic thio moieties are useful on a redox release carrier compound according to the invention. It is important that the silver ion complexing moiety be releasable from the redox release carrier. Selection of an optimum silver ion complexing moiety will depend upon such factors as the particular redox release carrier compound, the particular photographic silver halide capable of forming an internal latent image, processing conditions, the particular photographic silver halide capable of forming a surface latent image, pAg of the silver ion complex formed, solubility of the silver ion complexing moiety, and strength of complexing bond between the silver ion and complexing moiety. The silver ion complexing moiety is preferably a 1,2,4-triazolium-3-thio moiety that is capable of being released upon oxidation of the redox release carrier.

It is important that release of the silver ion complexing moiety occur much more rapidly from the oxidized form of the redox releasing carrier compound than from the reduced form. The rate determining step of silver ion complexing moiety released from the oxidized form of the adduct may be either the addition of a nucleophile, such as sulfite, to the oxidized adduct or the release rate of the silver ion complexing moiety from the nucleophilic adduct. The redox properties of the redox release carrier compound can influence the release rate and is a factor to be considered in selection of an optimum compound. It is important that the silver ion complexing moiety be released from the oxidized form of the redox release carrier compound in areas which have been exposed to light.

The redox release carrier compound may be oxidized either directly at silver latent image sites on the surface sensitive silver halide grains or through crossoxidation by the oxidized form of the primary developing agent. It is important that the released silver ion complexing moiety then uncover the internal image centers of the internally sensitive emulsion and permit development of these centers to produce enhanced silver images.

Unlike other silver halide compositions comprising a mixture of surface and internally sensitive emulsions the photographic materials of the present invention do not require high iodide emulsions to produce the desired silver enhancement. An iodide containing silver halide emulsion is not required in a photographic material according to the invention.

Examples of preferred silver ion complexing moieties which are useful according to the invention include:
1,4,5-trimethyl-1,2,4-triazolium-3-thiolate;
5-amino-2-mercapto-1,3,4-thiadiazole;
4-hydroxy-2-mercaptopyrimidine;
4,6-dihydroxy-2-mercaptopyrimidine;
5-hydroxymethyl-4-methyl-1,2,4-triazoline-3-thione;
1-(2-hydroxyethyl)-1,2,3,6-tetrahydro-1,3,5-triazine-5-thione; and
2-mercapto-5-methylureido-1,3,4-thiadiazole.

A range of redox release carrier compounds comprising the silver ion complexing moieties are useful according to the invention. The redox release carrier compound is preferably a silver halide developing agent or silver halide developing agent precursor. A highly preferred redox release carrier compound is a phenolic silver halide developing agent comprising the described silver ion complexing moiety. Examples of such phenolic silver halide developing agents are represented by the formulas:

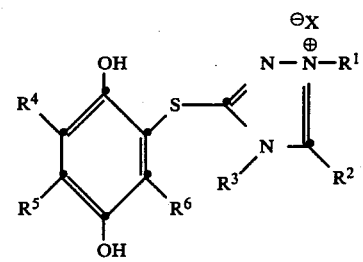

and

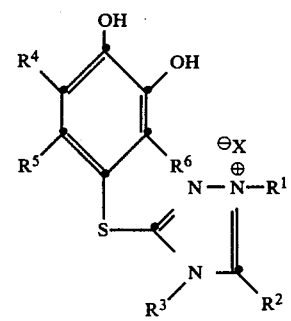

wherein:

$R^1$, $R^2$ and $R^3$ are individually alkyl, such as alkyl containing 1 to 25 carbon atoms, for instance, methyl, ethyl, propyl, butyl, pentyl, eicosyl and pentacosyl; alkenyl, such as alkenyl containing 2 to 25 carbon atoms, for instance, —CH=CH$_2$, —CH=CH—CH$_3$, —CH=CH—CH=CH$_2$ and —CH=CH—CH=CH—CH$_2$CH$_3$; aryl, preferably aryl containing 6 to 25 carbon atoms, such as phenyl and naphthyl; alkoxy, preferably alkoxy containing 1 to 25 carbon atoms, such as methoxy, ethoxy, decyloxy, and pentacosyloxy; or an amine group, such as represented by the structure

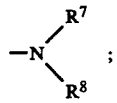

$R^4$, $R^5$ and $R^6$ are individually hydrogen; alkyl, such as alkyl containing 1 to 25 carbon atoms, for example methyl, ethyl, propyl, butyl and eicosyl; alkoxy, such as alkoxy containing 1 to 25 carbon atoms, for example methoxy, ethoxy and propoxy; sulfamyl; halo, such as bromo and chloro; or $R^4$ and $R^5$ taken together are the atoms necessary to complete a (i) carbocyclic ring, such as a benzo ring, or (ii) a heterocyclic ring, such as a 5 or 6 member heterocyclic ring, for example a pyrimidino, imidazolino or pyrazino ring;

$R^7$ is hydrogen or alkyl, preferably alkyl containing 1 to 25 carbon atoms, such as methyl, ethyl, propyl, decyl, eicosyl and pentacosyl;

$R^8$ is hydrogen; alkyl, preferably alkyl containing 1 to 25 carbon atoms, such as methyl, ethyl, propyl, butyl, decyl, eicosyl and pentacosyl; or aryl, preferably aryl containing 6 to 25 carbon atoms, such as phenyl and naphthyl; and X is an anion, such as p-toluenesulfonate; nitrate; trifluoroacetate; tetrafluoroborate; bromide; iodide; chloride; and, sulfate.

Another example of such a redox release carrier compound comprising a silver ion complexing moiety is a silver halide developing agent represented by the formula:

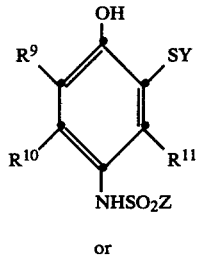

or

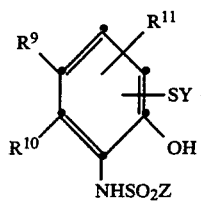

wherein:

Y is a silver ion complexing moiety capable of being released upon oxidation of the phenolic moiety;

Z is a substituent that does not adversely affect the redox release carrier compound or the silver ion complexing moiety; for example alkyl, such as alkyl containing 1 to 25 carbon atoms, for example methyl, ethyl, propyl, butyl, eicosyl and pentacosyl; or aryl, such as aryl containing 6 to 25 carbon atoms, for example phenyl, 2,4,5-triisopropylphenyl and naphthyl;

$R^9$, $R^{10}$ and $R^{11}$ are individually hydrogen; alkyl, such as alkyl containing 1 to 25 carbon atoms, for example methyl, ethyl, propyl, butyl, eicosyl and pentacosyl; alkoxy, such as alkoxy containing 1 to 25 carbon atoms, for example methoxy and propoxy; sulfamyl; halo, such as bromo and chloro; or $R^9$ and $R^{10}$ taken together are the atoms necessary to complete (i) a carbocyclic ring, such as a benzo ring, or (ii) a heterocyclic ring, such as a 5 or 6 member heterocylic ring, for example a pyrimidino, imidazolino or pyrazino ring;

Y is preferably a 1,2,4-triazolium-3-thio moiety, such as

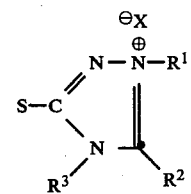

wherein X, $R^1$, $R^2$ and $R^3$ are as defined. Such compounds wherein Y is a 1,2,4-triazolium-3-thio moiety are new redox release carrier compounds.

Preferred redox release carrier compounds, which are also silver halide developing agents, are:

(a) 4-[1,4,5-trimethyl-1,2,4-triazolium-3-thio]-1,2-naphthalenediol p-toluenesulfonate;

(b) 2-[1,4,5-trimethyl-1,2,4-triazolium-3-thio]-1,4-dihydroxy-5,8-ethano-5,8-dihydronaphthalene p-toluenesulfonate;

(c) 2-[1,4,5-trimethyl-1,2,4-triazolium-3-thio]-1,4-dihydroxy-5,6-dimethylbenzene tetrafluoroborate;

(d) 2-[1,4,5-trimethyl-1,2,4-triazolium-3-thio]-1,4-dihydroxy-5,8-ethano-5,6,7,8-tetrahydronaphthalene p-toluenesulfonate; and, (e) 2-[1,4,5-trimethyl-1,2,4-triazolium-3-thio]-1,4-norbornanehydroquinone tetrafluoroborate;

and combinations of these silver halide developing agents.

Examples of redox release carrier compounds which are capable upon oxidation of imagewise releasing a silver ion complexing moiety are as follows:

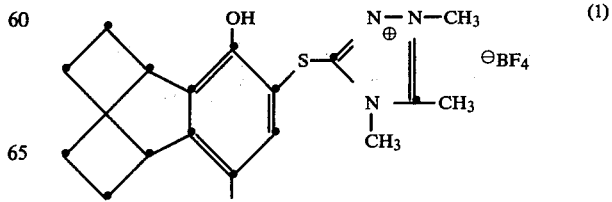

-continued
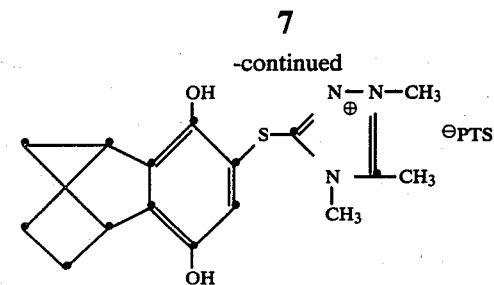 (2)
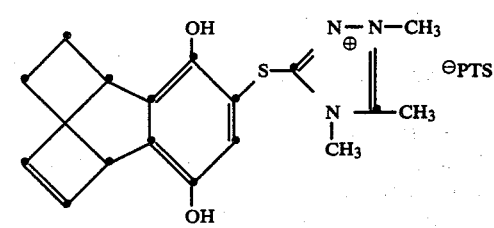 (3)
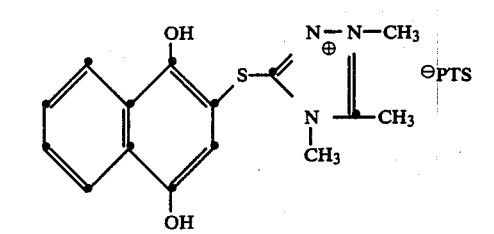 (4)
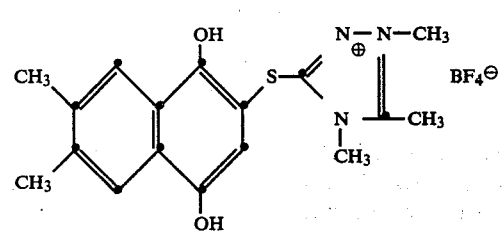 (5)
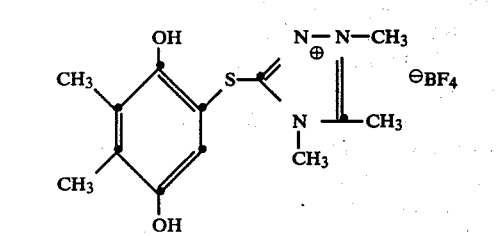 (6)
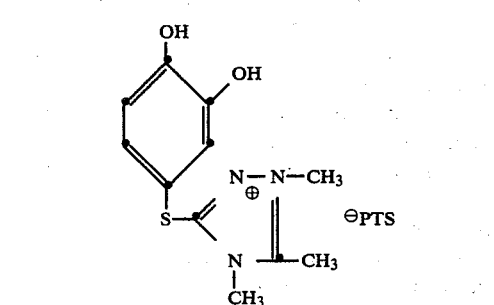 (7)
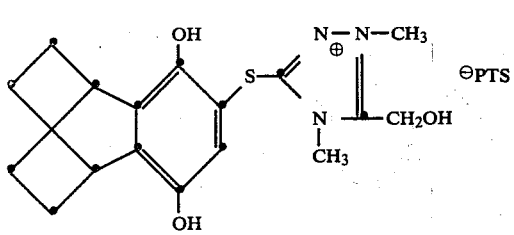 (8)
-continued
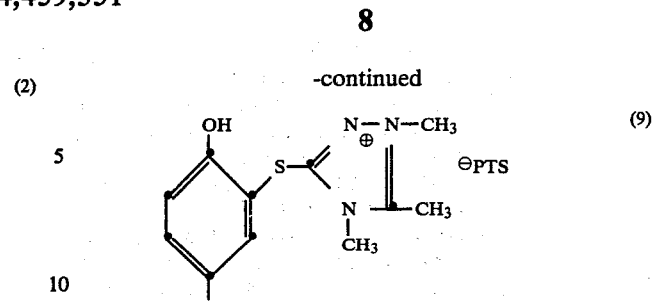 (9)
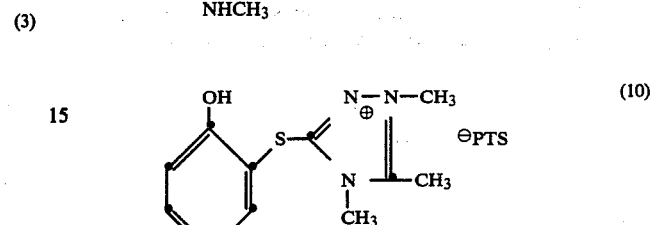 (10)
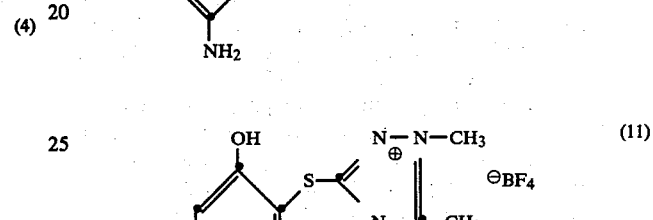 (11)
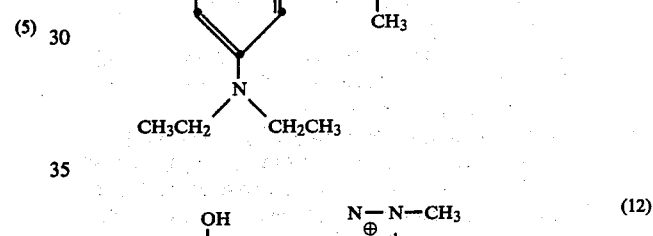 (12)
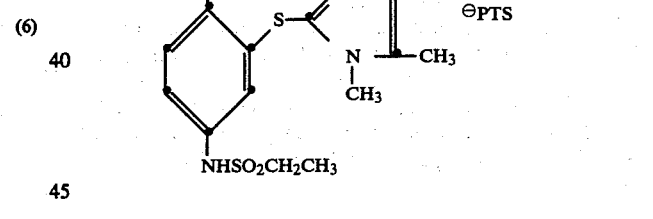 (13)
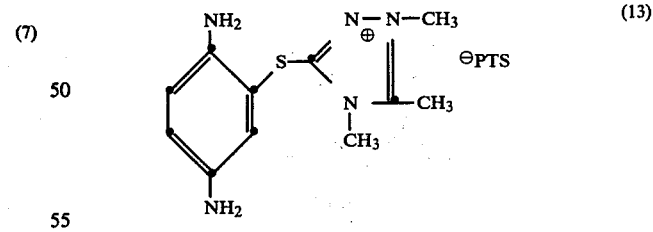 (14)
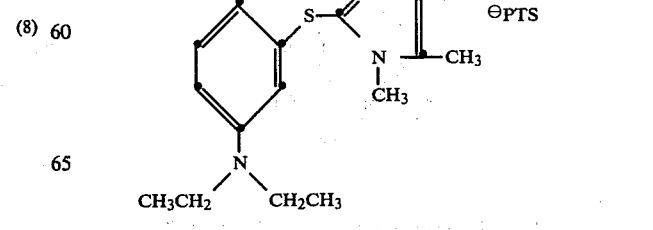

-continued
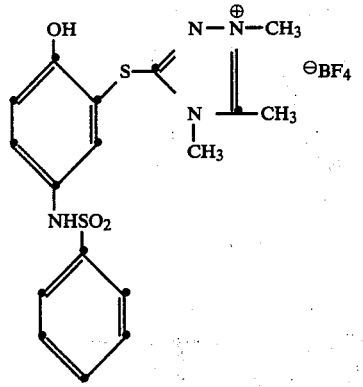 (15)
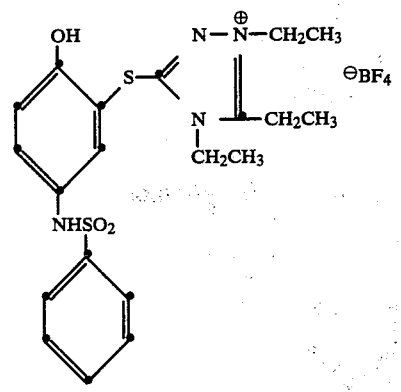 (16)
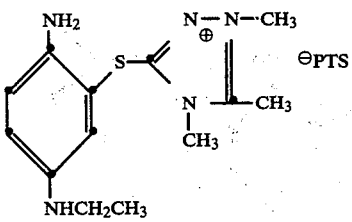 (17)
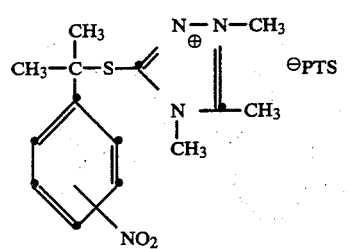 (18)
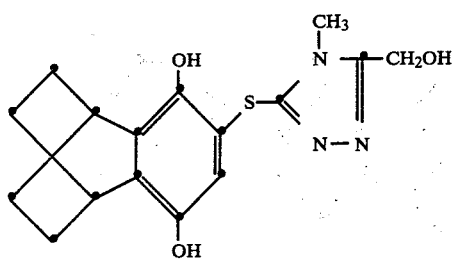 (19)
-continued
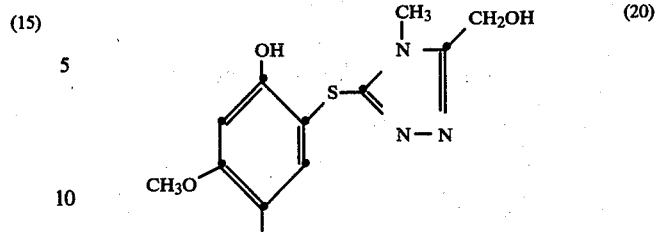 (20)
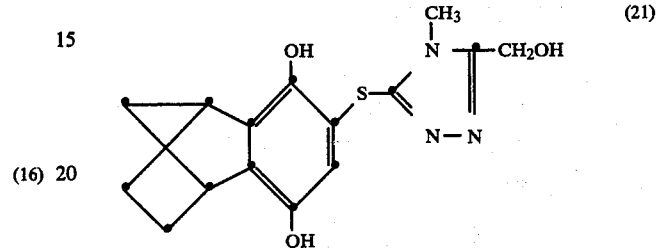 (21)
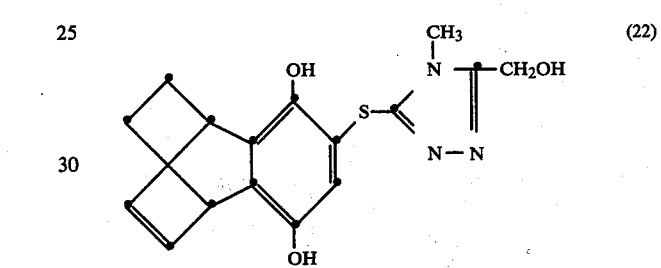 (22)
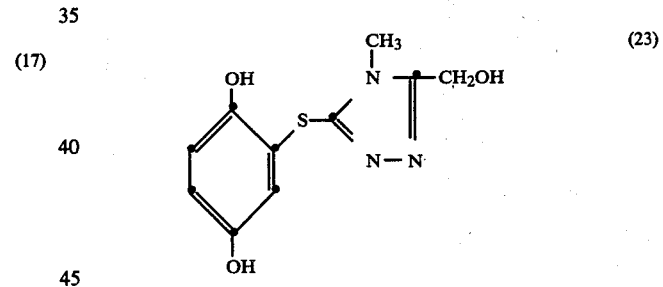 (23)
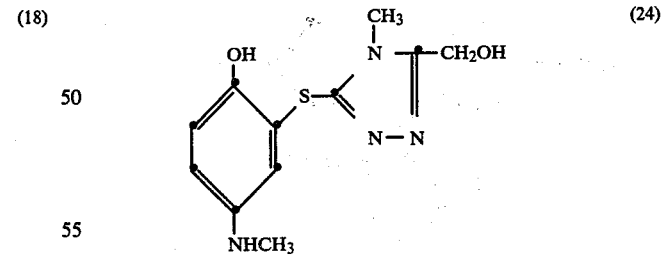 (24)
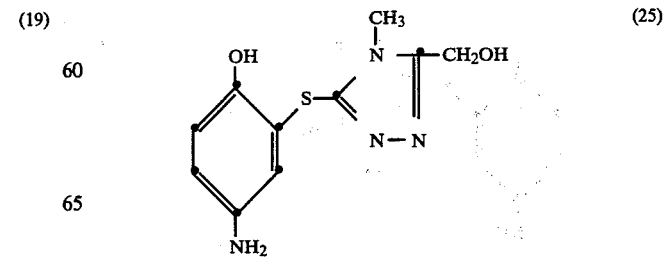 (25)

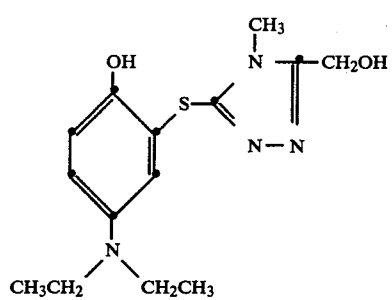 (26)
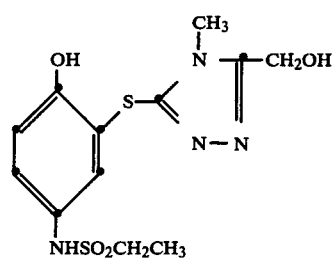 (27)
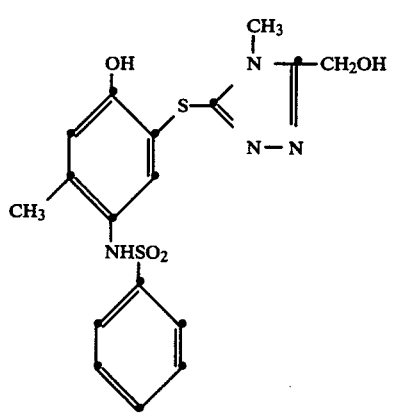 (28)
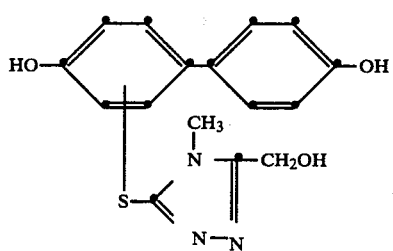 (29)
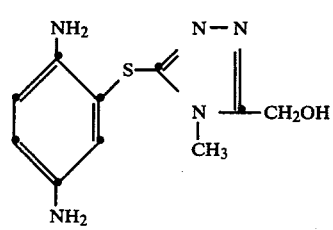 (30)
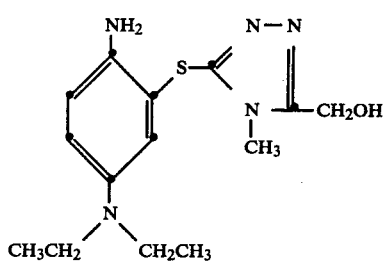 (31)
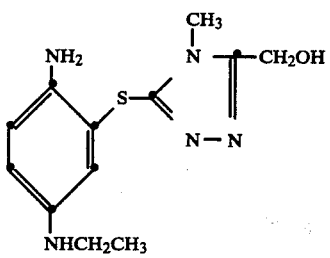 (32)
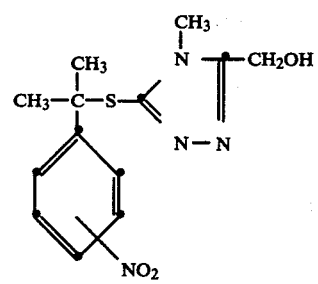 (33)
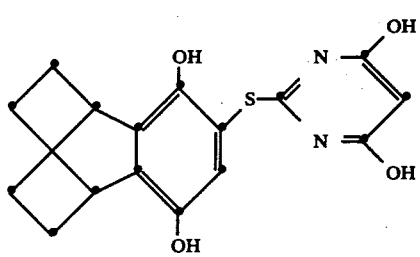 (34)
(35)
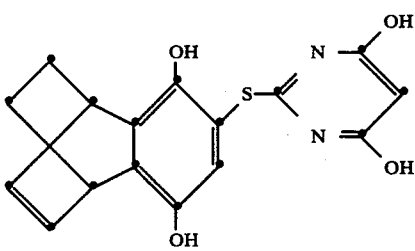 (36)

-continued
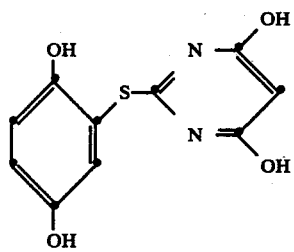 (37)
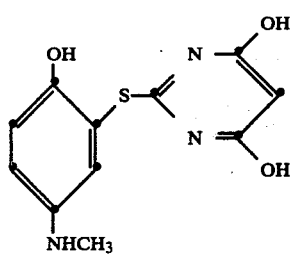 (38)
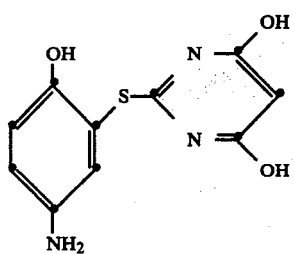 (39)
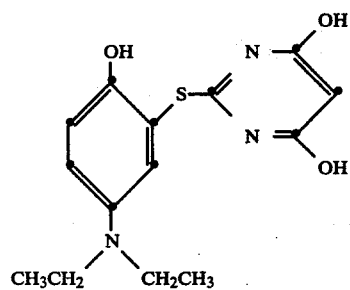 (40)
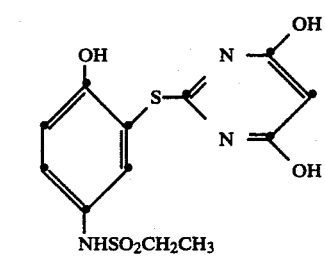 (41)
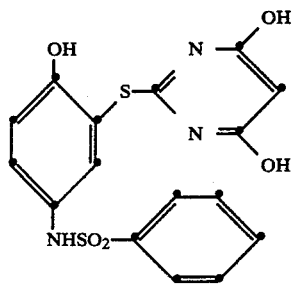 (42)
-continued
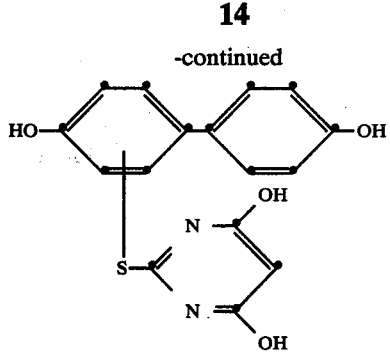 (43)
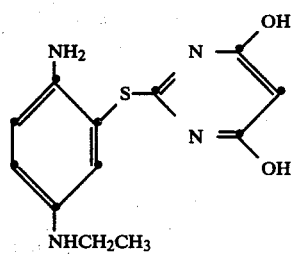 (44)
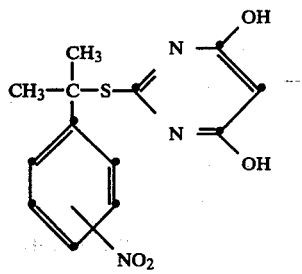 (45)
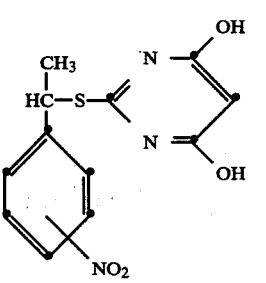 (46)
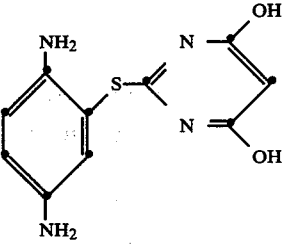 (47)
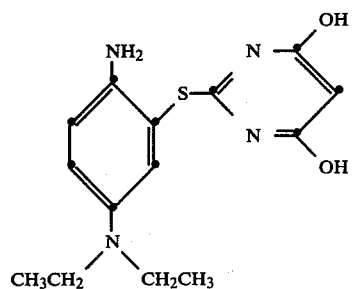 (48)

-continued

-continued

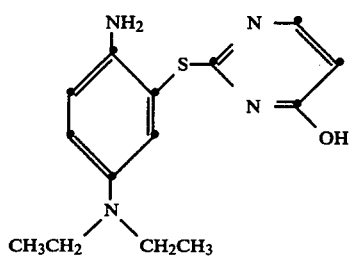 (77)
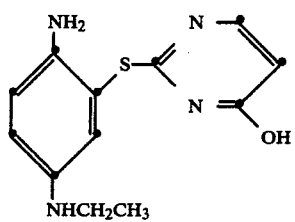 (78)
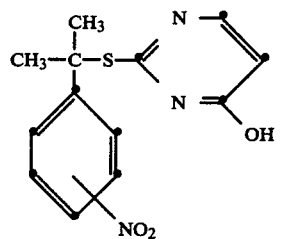 (79)
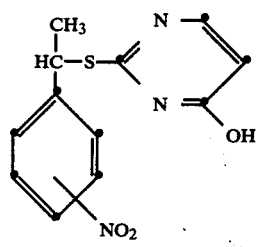 (80)
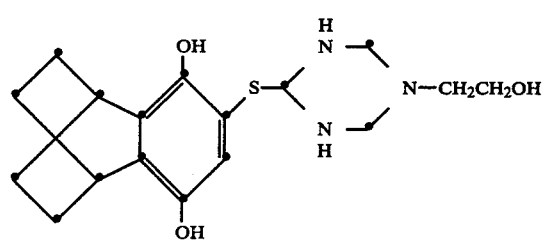 (81)
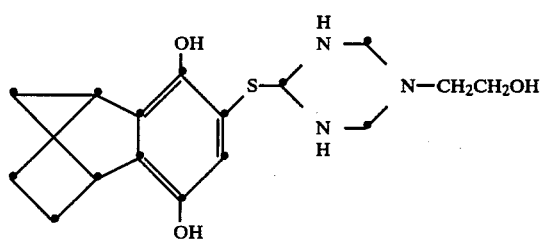 (82)
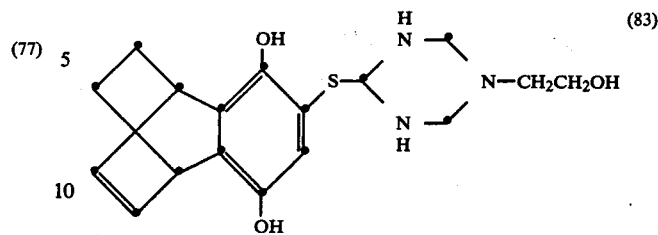 (83)
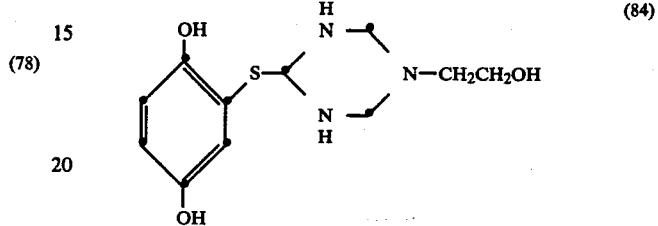 (84)
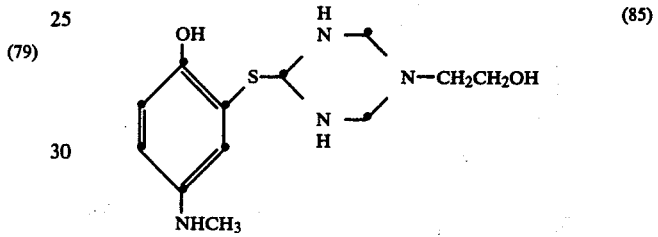 (85)
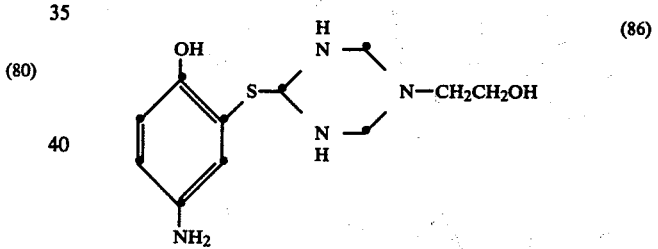 (86)
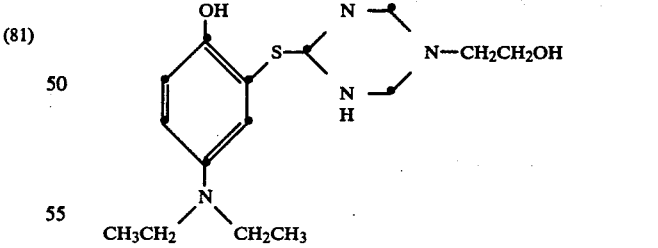 (87)
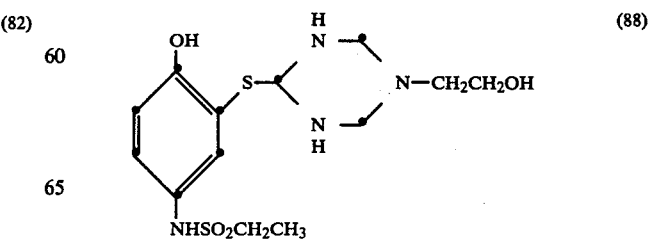 (88)

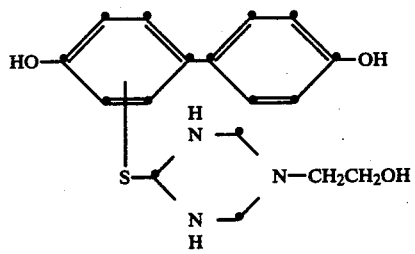 (89)
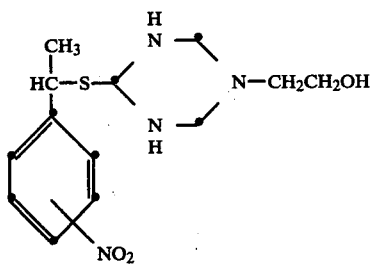 (95)
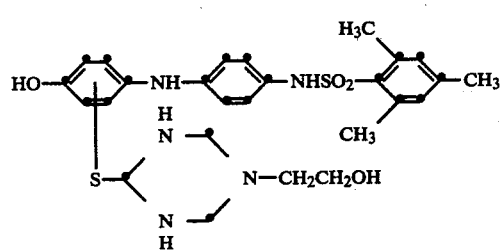 (90)
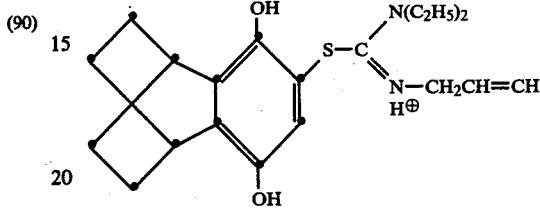 (96)
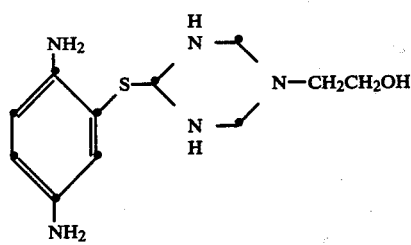 (91)
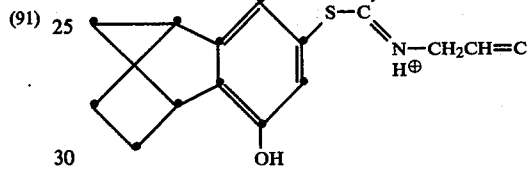 (97)
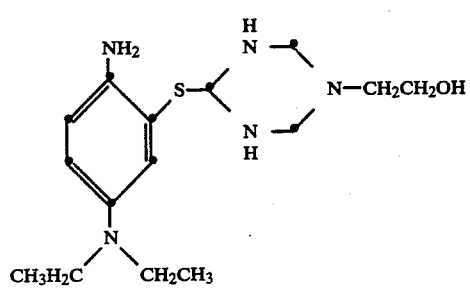 (92)
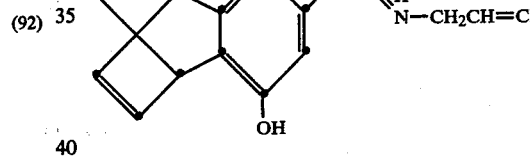 (98)
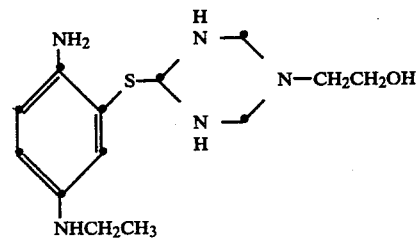 (93)
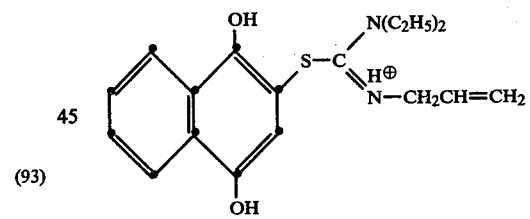 (99)
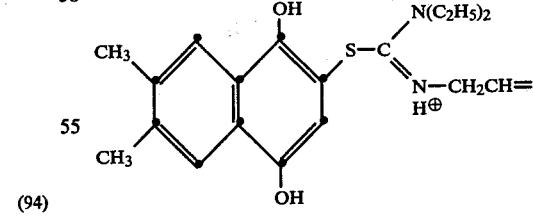 (100)
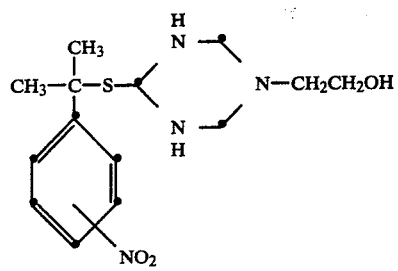 (94)
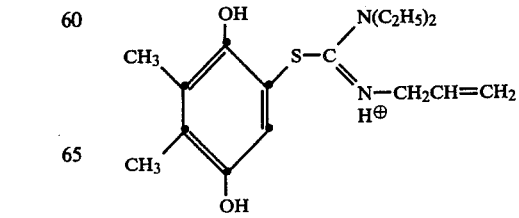 (101)

-continued
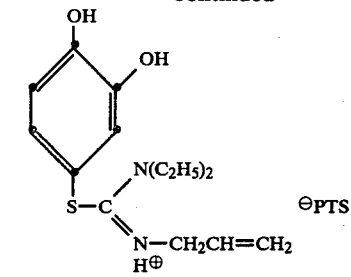 (102)
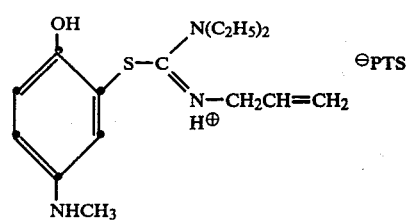 (103)
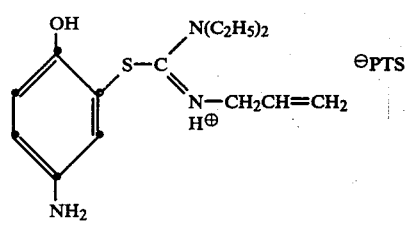 (104)
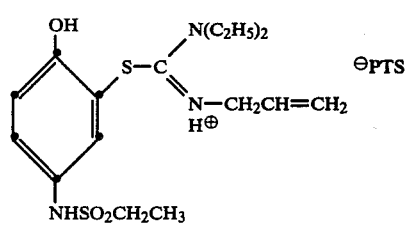 (105)
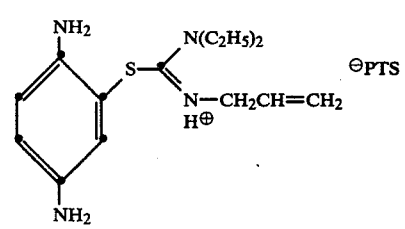 (106)
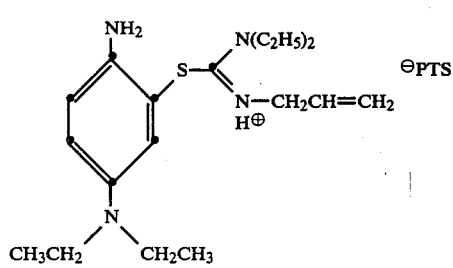 (107)
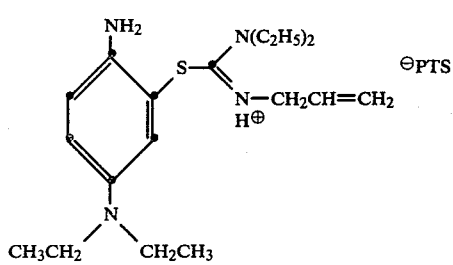 (108)
-continued
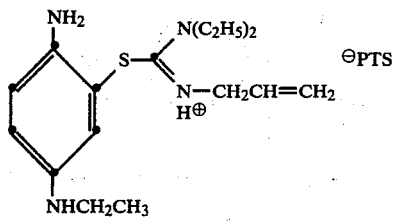 (109)
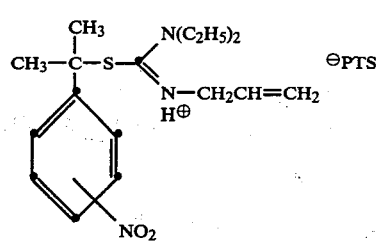 (110)
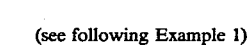
(see following Example 1)
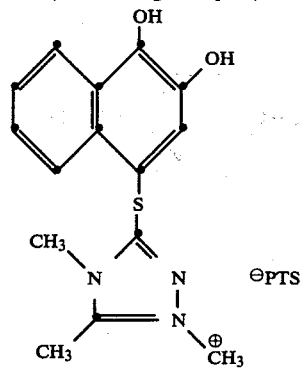 (111)
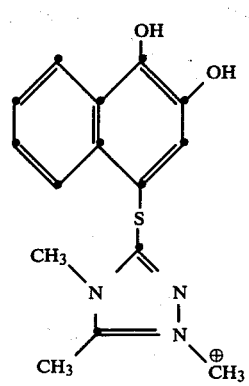 (112)
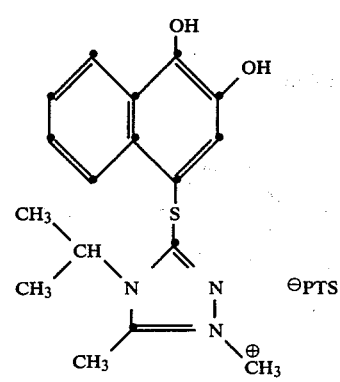 (113)

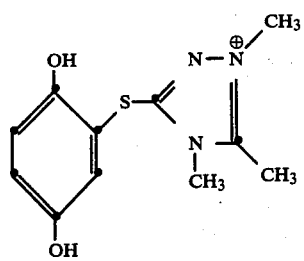 (114)
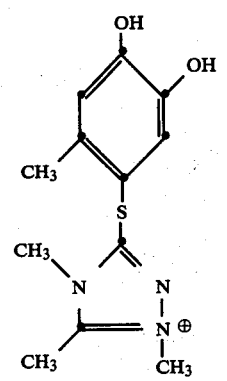 (115)
(see following Example 2)
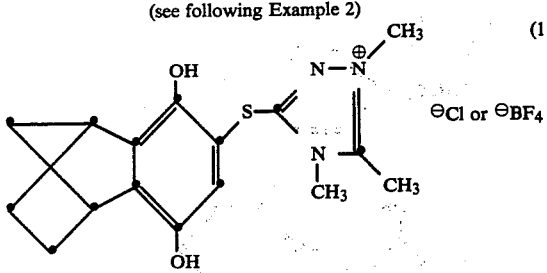 (116)
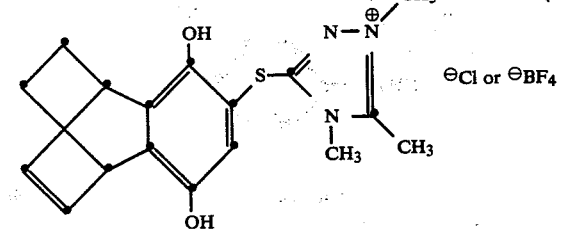 (117)
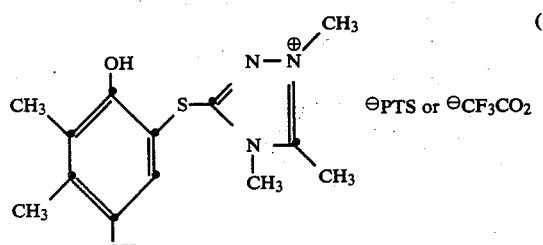 (118)
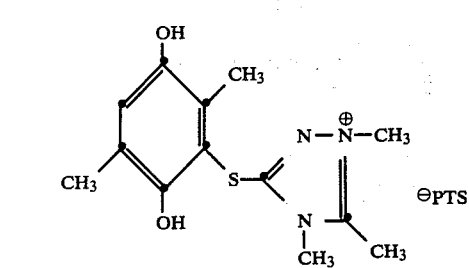 (119)
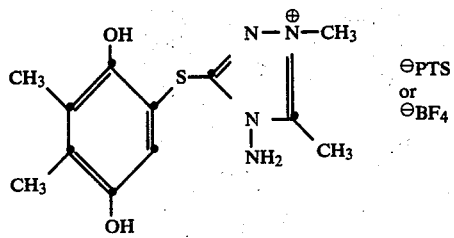 (120)
(121)
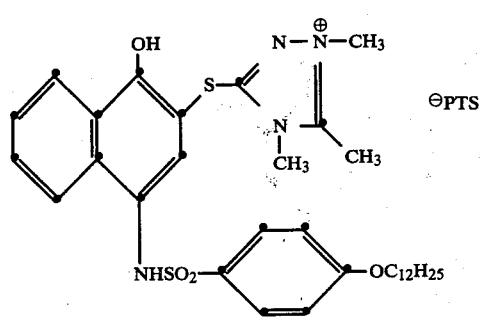 (122)
(123)
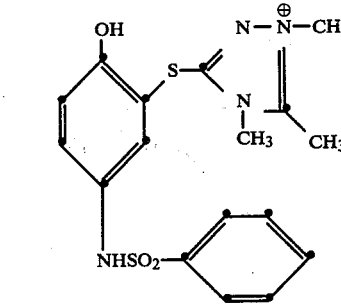 (124)

-continued
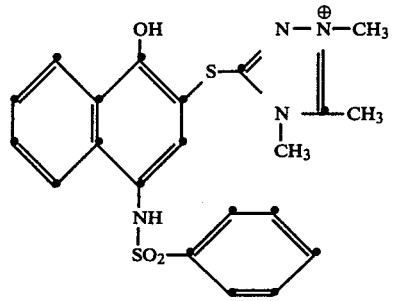 (125)
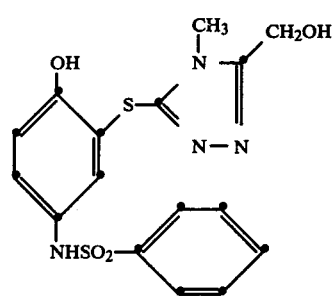 (126)
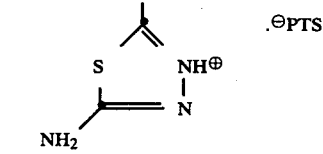 (127)
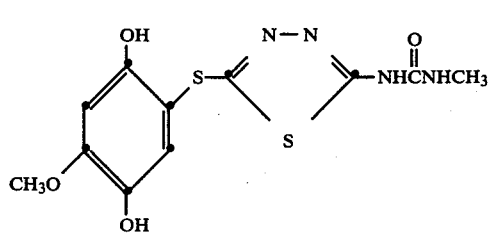 (128)
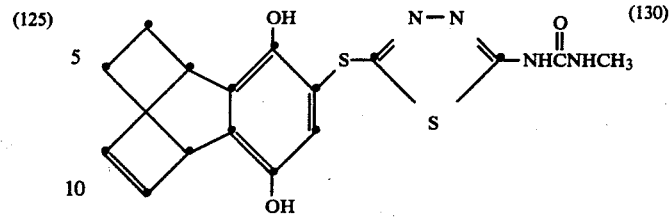 (129)
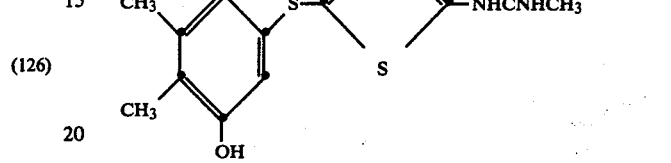 (130)
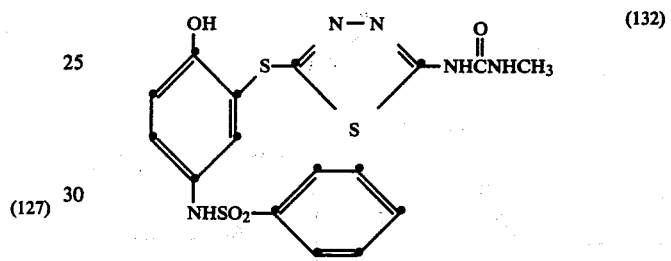 (131)
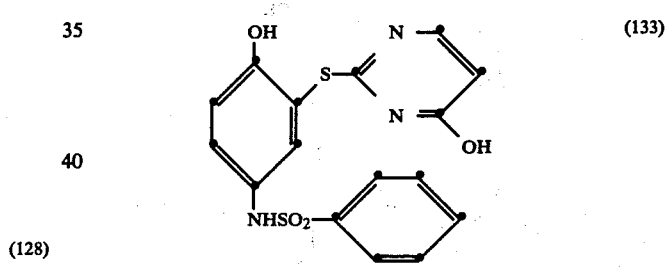 (132)
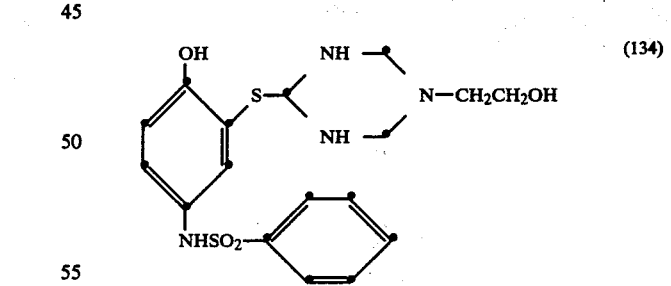 (133)
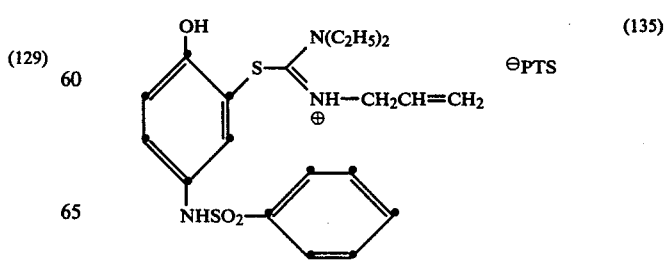 (134)
(135)

-continued

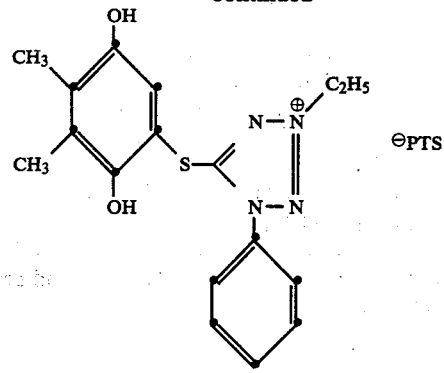
(136)

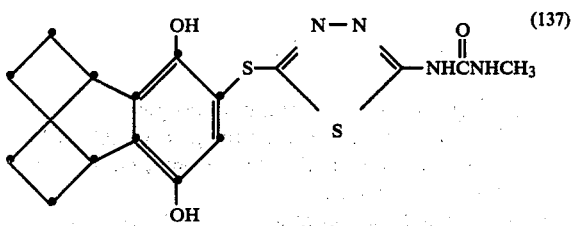
(137)

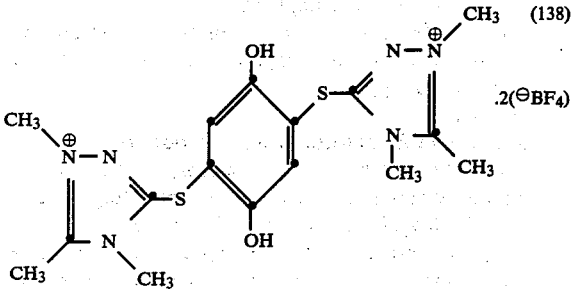
(138)

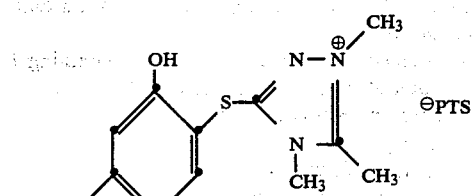
(139)

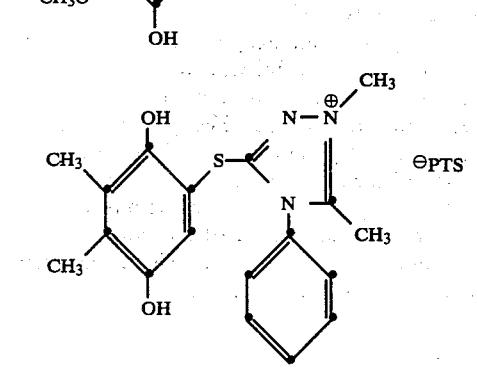
(140)

PTS herein means para-toluenesulfonate.

The methylureidothiadiazole compounds can be present either as their exocyclic isomers or as their endocyclic isomers.

The redox release carrier compounds which comprise a 1,2,4-triazolium-3-thio moiety are prepared, for example, by reacting a para or orthoquinone or a quinoneimine with a 1,2,4-triazolium-3-thiolate in the presence of a strong acid, such as p-toluenesulfonic acid, tetrafluoroboric acid, trifluoroacetic acid, nitric acid and hydrochloric acid, in a protic solvent, such as methanol, water, ethanol and mixtures of aprotic solvents and protic acids such as acetonitrile/trifluoroacetic acid or tetrahydrofuran/tetrafluoroboric acid. This reaction is generally known as a Michael addition.

The silver ion complexing moieties are prepared by procedures known in the organic compound synthesis art. For example, the 1,2,4-triazolium-3-thiolate compounds are prepared by procedures described in, for instance, Journal of Organic Chemistry, Volume 32, pages 2245 and following (1967) by K. T. Potts, S. K. Roy and D. P. Jones.

The quinone and quinoneime compounds, such as the benzoquinones, naphthoquinones, quinoneimines and naphthoquinoneimes, from which the preferred redox release compounds are prepared, are available from commercial sources or are prepared from readily available starting materials by methods known in the organic compound synthesis art. For example, certain quinones can be prepared by oxidizing the corresponding hydroquinone compounds as described in, for example, Australian Journal of Chemistry, Vol. 31, pages 347 and following (1978), by L. Gurd. Others can be prepared by oxidation of the corresponding amino phenol compounds.

An example of a preparation of a quinone compound useful as a starting material for preparation of a redox release compound according to the invention is the preparation of 5,8-ethano-5,6,7,8-tetrahydro-1,4-naphthoquinone represented by the structure:

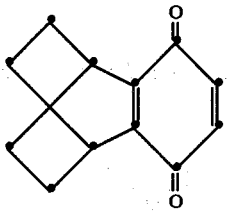

In this preparation 0.054 mole (10.0 g) of 5,8-ethano-5,6-dihydro-1,4-naphthoquinone is hydrogenated by means of platinum/carbon in tetrahydrofuran to provide the corresponding 5,6,7,8-tetrahydro-1,4-dihydroxynaphthalene (melting point of 213°–215° C.). 0.05 Mole (9.0 g) of the 1,4-dihydroxynaphthalene compound is dissolved in 200 ml of aqueous ethanol (50:50 volume by volume). To this is added a solution containing 27.0 g of FeCl$_3$.6H$_2$O, 200 ml of water and 50 ml of hydrochloric acid. A dark solid slowly forms during ½ hour of stirring at room temperature (about 20° C.). After the solid is collected by filtration, it is recrystallized from a mixture of 150 ml of hot water (80° C.) and 50 ml of ethanol. Upon cooling to room temperature (about 20° C.), crystallization commences. 5.5 Grams of dark needles are obtained of the desired product having a melting point of 140°–142° C.

Another example of a preparation of a starting material according to the invention is the preparation of norbornane-p-benzoquinone represented by the structure:

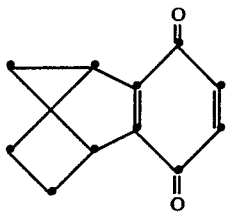

According to this preparation, silver (I) oxide (50.0 g, 0.22 mole) is added to a stirred acetone (500 ml) suspension of norbornane-p-hydroquinone (12.1 g, 0.069 mole) and the mechanically stirred dark suspension is refluxed on the steam bath for 1 hour. The cooled suspension is filtered through Celite and the solvent in the red eluate is removed under reduced pressure. The residual red oil is crystallized with ethyl ether-hexane. This provides the desired product having a melting point of 45° C. and identified by mass spectral analysis.

A preferred method is a method of preparing an aromatic diol compound containing a silver ion complexing 1,2,4-triazolium-3-thio moiety, as described, that is capable of being released upon oxidation of the diol compound, wherein the method comprises the step of reacting a mesoionic compound represented by the formula:

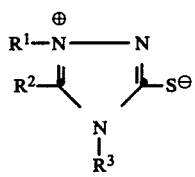

with a quinone compound represented by the formula:

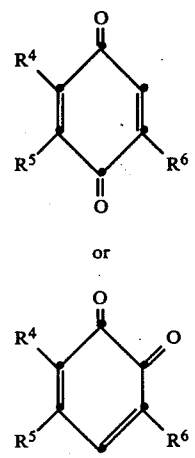

wherein the reaction is carried out in a protic solvent in the presence of an acid represented by the formula:

HX wherein:
X is an anion, such as tetrafluoroborate, p-toluenesulfonate, nitrate, chloride and trifluoroacetate; and, wherein:

$R^1$, $R^2$ and $R^3$ are individually alkyl, preferably alkyl containing 1 to 25 carbon atoms, such as methyl, ethyl, propyl, butyl, eicosyl and pentacosyl;

alkenyl, preferably alkenyl containing 2 to 25 carbon atoms, such as —CH=CH$_2$, —CH=CH—CH$_3$, —CH=CH—CH=CH$_2$ and —CH=CH—CH=CH—CH$_2$CH$_3$;

aryl, preferably aryl containing 6 to 25 carbon atoms, such as phenyl and naphthyl;

alkoxy, preferably alkoxy containing 1 to 25 carbon atoms such as methoxy, ethoxy, decyloxy and pentacosyloxy; or

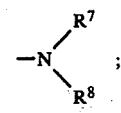

$R^4$, $R^5$ and $R^6$ are individually hydrogen;

alkyl, preferably alkyl containing 1 to 25 carbon atoms, such as methyl, ethyl, propyl, butyl, decyl, eicosyl and pentacosyl;

aryl, preferably aryl containing 6 to 25 carbon atoms, such as phenyl and naphthyl;

alkoxy, preferably alkoxy containing 1 to 25 carbon atoms, such as methoxy, ethoxy, decyloxy and pentacosyloxy;

sulfamyl;

halo, preferably chloro, bromo or iodo; or $R^4$ and $R^5$ together are the atoms, preferably the atoms selected from the group consisting of carbon, hydrogen, oxygen, and nitrogen atoms, necessary to complete a (i) carbocyclic ring, such as a norbornane ring, or (ii) a 5 or 6 member heterocyclic ring, such as a pyridino, pyrazino, pyrimidino or imidazolino ring;

$R^7$ is hydrogen or alkyl, preferably alkyl containing 1 to 25 carbon atoms, such as methyl, ethyl, propyl, butyl, decyl, eicosyl and pentacosyl;

$R^8$ is hydrogen;

alkyl, preferably alkyl containing 1 to 25 carbon atoms, such as methyl, ethyl, propyl, butyl, decyl, eicosyl and pentacosyl; or aryl, preferably aryl containing 6 to 25 carbon atoms, such as phenyl and naphthyl; and X is an anion, such as tetrafluoroborate, p-toluenesulfonate, nitrate and halide. The protic solvent is preferably a compound selected from the group consisting of methanol, ethanol and water.

The quinone compound can be generated in situ. The quinone compounds can be isolated if desired.

A highly preferred method of preparing an aromatic diol compound represented by the formula:

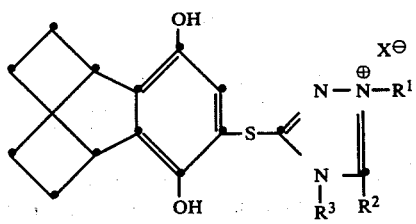

or

-continued

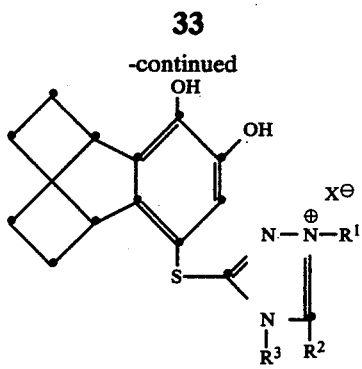

is the method comprising the step of reacting a mesoionic compound represented by the formula:

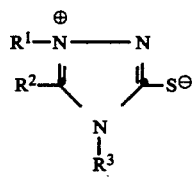

with a quinone compound represented by the formula:

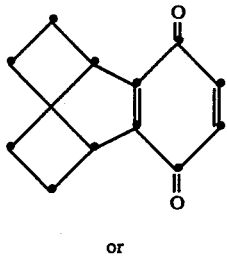

or

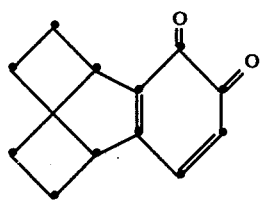

wherein the reaction is carried out in a protic solvent in the presence of an acid represented by the formula:

HX wherein:
X is an anion; and wherein:
$R^1$, $R^2$, $R^3$, $R^7$, $R^8$ and X are as defined.

An illustrative method of preparing a compound according to the invention is the preparation of 4-[1,4,5-trimethyl-1,2,4-triazolium-3-thio]-1,2-naphthalenediol p-toluene sulfonate. This method comprises the step of reacting (a) 1,2-naphthoquinone with (b) 1,4,5-trimethyl-1,2,4-triazolium-3-thiolate and (c) p-toluenesulfonic acid in water at about 18° C. to about 25° C. Another illustrative method is the method of preparing 2-[1,4,5-trimethyl-1,2,4-triazolium-3-thio]-1,4-norbornanehydroquinone tetrafluoroborate. This method comprises the step of reacting (a) norbornane-p-benzoquinone with (b) 1,4,5-trimethyl-1,2,4-triazolium-3-thiolate with (c) tetrafluoroboric acid in methanol at about 18° C. to about 25° C.

Another illustrative method of preparing a compound according to the invention is the preparation of a sulfonamidophenol or sulfonamidonaphthol compound containing a silver ion complexing 1,2,4-triazolium-3-thio moiety that is capable of being released upon oxidation of the sulfonamidophenol or sulfonamidonaphthol compound. This illustrative method comprises the step of reacting a mesoionic compound represented by the formula:

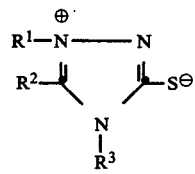

with a quinoneimine compound represented by the formula:

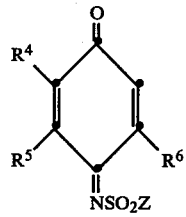

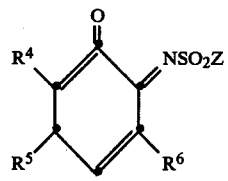

wherein said reaction is carried out in a protic solvent in the presence of an acid represented by the formula HX wherein X is an anion as defined and wherein Z, $R^1$, $R^2$, $R^3$, $R^4$, $R^5$ and $R^6$ are as defined above.

The photographic silver halides according to the invention comprise silver halides known in the photographic art. The photographic silver halides include, for example, silver bromide, silver chloride, silver chlorobromide, silver chloroiodide, silver bromoiodide, silver chlorobromoiodide or mixtures thereof. The photographic silver halide includes coarse, medium or fine grain silver halide bounded by 100, 111 or 110 crystal planes and can be prepared by a variety of techniques such as single jet, double jet (including continuous removal techniques), accelerated flow rate and interrupted precipitation techniques known in the photographic art. The photographic silver halides are also, for example, tabular grain photographic silver halides. The silver halides and their preparation are as described in, for example, *Research Disclosure*, December 1978, Item No. 17643.

The silver halides are either monodispersed or polydispersed as precipitated. The grain size distribution is controlled by silver halide grain separation techniques or by blending silver halide emulsions of differing grain sizes. The emulsions include Lippman emulsions and ammoniacal emulsions; excess halide ion ripened emulsions; thiocyanate ripened emulsions; thioether ripened emulsions; or emulsions containing weak silver halide solvents, such as ammonium salts. The silver halide emulsions are unwashed or washed to remove soluble salts. The soluble salts are removed by, for example, chill setting and leaching; by coagulation washing; by centrifugation and decantation of a coagulated emulsion; by employing hydrocyclones alone or in combination with centrifuges; by diafiltration with a semipermeable membrane; or by employing an ion exchange resin. The emulsions, with or without sensitizers, can be dried and stored prior to use as known in the photographic art.

The silver halides are generally chemically sensitized by means known in the photographic art. Such chemical sensitization can be by means of active gelatin, or sulfur, selenium, tellurium, gold, palladium, platinum, iridium, osmium, rhodium or phosphorous sensitizers or combinations of such sensitizers. Other means of chemical sensitization, such as described in *Research Disclosure*, December 1978, Item No. 17643, paragraph III are also useful.

The photographic silver halides comprise addenda known to be useful in the photographic art as described in *Research Disclosure*, December 1978, Item No. 17643. Such addenda include, for example, spectral sensitizing dyes, brighteners, antifoggants and emulsion stabilizers, light absorbing and scattering dyes, hardeners, coating aids, plasticizers and lubricants, matting agents, development modifiers, and the like.

The photographic silver halides capable of forming a surface image are silver halides that upon exposure form latent images primarily on the surfaces of the silver halide grain, not in the interior of the grain. For example, the photographic silver halides capable of forming a surface image are photographic silver halides which when measured according to normal photographic testing techniques by coating a test portion of the photographic silver halide emulsion on a transparent support, exposing the test portion to a light intensity scale for a fixed time between 0.01 and 1 second and development for 6 minutes at 68° F. (20° C.) in a developer A as herein defined, have a sensitivity, measured at a density of 0.1 above fog, greater than the sensitivity of an individual test portion of the same emulsion which has been exposed in the same way, bleached 5 minutes in aqueous 0.3% potassium ferricyanide solution at 65° F. (18.5° C.), and developed for 5 minutes at 65° F. (18.5° C.) in developer B as herein defined. Developer A is the general type of surface image developer known to be useful in the photographic art and developer B is an internal developer having high silver halide solvent activity. Such photographic silver halides capable of forming a surface image are described in, for example, U.S. Pat. No. 3,178,282; U.S. Pat. No. 2,996,382; U.S. Pat. No. 3,695,881 and *Research Disclosure*, December 1978, Item No. 17643.

Developer A as described herein comprises the following components:

|  | Grams |
| --- | --- |
| N—methyl-p-aminophenol sulfate | 0.31 |
| Sodium sulfite, desiccated | 39.6 |
| Hydroquinone | 6 |
| Sodium carbonate, desiccated | 18.7 |
| Potassium bromide | 0.86 |
| Citric acid | 0.68 |
| Potassium metabisulfite | 1.5 |
| Water to make 1 liter | |

The developer B as described herein comprises the following components:

|  | Grams |
| --- | --- |
| N—methyl-p-aminophenol sulfate | 2.0 |
| Sodium sulfite, desiccated | 90 |
| Hydroquinone | 8.0 |
| Sodium carbonate, monohydrate | 52.5 |
| Potassium bromide | 5 |
| Sodium thiosulfate | 10 |
| Water to make 1 liter | |

The photographic silver halide capable of forming an internal latent image is one which when measured according to normal photographic techniques in its unfogged stage by coating a test portion of the emulsion on a transparent support, exposing to a light intensity scale for a fixed time between 0.01 and 1 second, bleaching 5 minutes in a 0.3% potassium ferricyanide solution at 65° F. (18.5° C.) and developing for about 5 minutes at 65° F. (18.5° C.) in developer B, as defined herein, has a sensitivity, measured at a density of 0.1 above fog, appreciably better, for instance 0.6 log E greater, than the sensitivity of an identical test portion which has been exposed in the same way and developed for 6 minutes at 68° F. (20° C.) in developer A, as defined. Useful photographic silver halides capable of forming an internal latent image are known in the photographic art and include those described in, for example, U.S. Pat. Nos. 2,592,250; 2,456,953; 3,206,313; 3,317,322; 3,367,778; 3,447,927; 3,957,488; 4,055,185; 3,923,513; 3,935,014; 3,850,637; 3,761,276 and *Research Disclosure*, December 1978, Item No. 17643, the disclosures of which are incorporated herein by reference.

An illustrative photographic silver halide capable of forming an internal image includes, for example, an unsensitized silver halide, also known as a primitive silver halide, which includes what is known in the photographic art as a halide converted silver halide, and a silver halide which has occluded foreign ion dopants.

The photographic silver halide capable of forming an internal latent image is preferably fogged, partly or completely, before use in a photographic material according to the invention.

Production of a photographic silver halide capable of forming an internal latent image according to the invention is carried out by means known in the photographic art. For example, in forming a photographic silver halide which is internally fogged, the fogging of the emulsion can be produced by merely exposing the emulsion to light or other methods known in the photographic art, such as chemical fogging methods. Fogging can also occur as a function of imagewise exposure of the photographic silver halide to light. The silver halide having high internal sensitivity can be prepared by fogging the photographic silver halide having both internal and surface sensitivity and then bleaching the surface image with a solution of potassium ferricyanide. Another means of obtaining photographic silver halide capable of forming an internal latent image is by exposure of non-fogged internal image emulsions to high energy radiation, such as x-rays. Photographic silver halides known in the photographic art as core/shell photographic silver halides are also useful.

The ratio of photographic silver halide capable of forming a surface image to photographic silver halide capable of forming an internal image in a photographic material according to the invention varies depending upon such factors as the types of photographic silver halide emulsions, the desired contrast of the image, processing conditions, other components in the photographic material, desired total density and the like. A generally useful ratio of photographic silver halide capable of forming a surface image to photographic silver halide capable of forming an internal image is, for example, within the range of about 5:1 to about 1:5. A highly preferred ratio is within the range of about 3:1 to about 1:2.

The redox release carrier compound containing a silver ion complexing moiety, the photographic silver halide capable of forming a surface image and the photographic silver halide capable of forming an internal image are in any location in the photographic material which enables the desired interaction of the components upon exposure and processing. All of the components are preferably in a single emulsion layer. However, the components can be coated in contiguous layers or in a separate carrier element which is laminated to the photographic silver halide containing layers during processing. In coating the two types of photographic silver halides in separate layers, either photographic silver halide can be coated in a layer farthest from the support. Optionally the photographic silver halide capable of forming a surface image and the silver halide capable of forming a internal latent image can be mixed as a blend and coated over a layer comprising the redox release carrier compound containing a silver ion complexing moiety. In another option the photographic silver halide capable of forming a surface image and a silver halide capable of forming an internal latent image can be mixed and coated over an emulsion layer comprising a fogged internal image of silver halide emulsion which can be identical to or different from the photographic silver halide capable of forming a internal latent image in the contiguous layer.

The various addenda, including the redox release carrier compound containing a silver ion complexing moiety, are incorporated into the layers of the photographic elements according to the invention by methods known in the photographic art. For example, the redox release carrier compound containing a silver ion complexing moiety can be dissolved and added prior to coating either from water or organic solvent solutions depending upon the solubility of the redox release carrier compound and other components in the material. Hydrophobic addenda can be mechanically dispersed directly or in high boiling solvents, also known as coupler solvents, or the hydrophobic addenda can be loaded into latices and dispersed in a vehicle.

In forming photographic elements according to the invention the layers are located on the photographic support by various procedures known in the photographic art, including immersion or dip coating, roller coating, reverse roll coating, air-knife coating, doctor blade coating, spray coating, extrusion coating, bead coating, stretch flow coating and curtain coating. Two or more layers can be coated simultaneously. Illustrative methods of coating are described in, for example, *Research Disclosure*, December, 1978, Item No. 17643.

The layers of the photographic elements according to the invention are coated on a variety of supports. Useful photographic supports include polymeric film, paper, metallic sheet and foil, glass and ceramic supporting elements provided with one or more subbing layers to enhance the adhesive, antistatic, dimensional, abrasive, hardness, frictional, antihalation and/or other properties of the support surface. Useful polymeric film supports are films of cellulose nitrate and cellulose esters such as cellulose triacetate and diacetate, polystyrene, polyamides, homo- and copolymers of vinyl chloride, poly(vinylacetal), polycarbonate, homo- and copolymers of olefins, such as polyethylene and polypropylene, and polyesters of dibasic aromatic carboxylic acids with divalent alcohols, such as poly(ethylene terephthalate). Other useful illustrative photographic supports are described in, for example, *Research Disclosure*, December 1978, Item No. 17643 in paragraph XVII.

The photographic materials according to the invention are imagewise exposed by means of various forms of energy known to be useful in the photographic art. These include, for example, the ultraviolet and visible and infrared regions of the electromagnetic spectrum as well as electron beam and $\beta$-radiation, gamma ray, x-ray, $\alpha$-particle, neutron radiation and other forms of corpuscular and wavelike radiant energy in either non-coherent (random phase) forms or coherent (in phase) forms, as produced by lasers. Exposures are monochromatic, orthochromatic or panchromatic. Imagewise exposure is at ambient, elevated or reduced temperatures and/or pressures, including high or low intensity exposures, continuous or intermittent exposures, exposure time ranging from minutes to relatively short durations in the milliseconds to microsecond range. Exposures are within the useful range of response determined by conventional sensitometric techniques for the photographic silver halides in the photographic material according to the invention.

The photographic materials according to the invention are processed after exposure to form a visible image by associating the photographic material with an a aqueous alkaline medium in the presence of a developing agent contained in the medium or the photographic material. Processing formulations and techniques that are useful are those known in the photographic art for developing an image and a photographic silver halide capable of forming a surface image. Such formulations and techniques include those described in *Research Disclosure*, December 1978, Item No. 17643, the disclosure of which is incorporated herein by reference. Optionally, an auxiliary silver halide developing agent is useful in order to provide added density upon processing. Such primary or auxiliary developing agents are selected from those described in for example, *Research Disclosure*, December 1978, Item No. 17643, paragraph XX. Illustrative classes of useful organic silver halide developing agents include hydroquinones, catechols, aminophenols, pyrazolidones, phenylenediamines, tetrahydroquinolines, cycloalkanones, pyrimidines, reductones, and coumarins. Useful inorganic developing agents include ferrous ion complexes and titanous ion complexes. The developing agents are present in one or more coated layers of the photographic element such as the silver halide emulsion layer or in a layer contiguous to the silver halide layer.

Developer compositions which cause general development of an internal latent image silver halide on development of a latent image in the surface image silver halides are to be avoided. Such developer compositions darken the entire photographic silver halide layer and no silver image is produced. Developer compositions should not contain addenda, such a potassium iodide which cause cracking of the internal silver halide grains unless the concentration of such addenda are maintained at very low levels.

Optimum imaging in a photographic material according to the invention relies on the relatively slow nonimagewise release of the silver ion complexing moiety from the unoxidized carrier molecule. When the redox release compound containing the silver ion complexing moiety in the photographic material is oxidized, either by direct redox reaction with the exposed photographic silver halide capable of forming a surface latent image, or through crossoxidation by the oxidized primary developing agent, the silver ion complexing moiety is rapidly released and exposes the internal latent image centers of the silver halide capable of forming an internal latent image. Sulfite significantly accelerates the rate of silver ion complexing moiety release, especially the release of a 1,2,4-triazolium-3-thio moiety, when compared with nucleophiles such as hydroxide. The exact mechanism for release of the silver ion complexing moiety is not fully understood. However, the much slower rate of 1,2,4-triazolium-3-thio moiety release from an unoxidized hydroquinone molecule is probably due to the slow breakdown of a sulfite addition intermediate. The concentration of sulfite in the developer composition is generally within the range of about 3 g to about 150 g per liter of developer composition. An optimum concentration of sulfite will depend upon such factors as the particular redox release compound, the particular silver ion complexing moiety, the silver halide capable of forming a surface latent image, the particular silver halide capable of forming an internal latent image, processing conditions, other addenda in the photographic material and their components of the developer composition.

An example of a developer composition that is useful according to the invention comprises the following:
$Na_2SO_3$: 72.0 g/liter
Elon: 5.0
Hydroquinone: 10.0
Kodalk (sodium metaborate): 35.0
KBr: 5.0
NaOH or KOH: to pH 10.45 @ 22° C.

The photographic materials according to the invention are useful for producing negative images or positive images. The procedure for producing a positive image is similar to that for providing a negative image with the exception that a direct-positive photographic silver halide is used which is capable of forming a sub-surface latent image.

In order to help provide lower silver coverage while producing the same developed density upon processing, the silver halide capable of forming an internal latent image should be of smaller grain size than the photographic silver halide capable of forming a surface latent image. This enables the silver halide capable of forming an internal latent image to have higher covering power. This is illustrated in the following examples. The following examples are included for a further understanding of the invention.

EXAMPLE 1

Preparation of
4-[1,4,5-trimethyl-1,2,4-triazolium-3-thio]-1,2-naphthalenediol p-toluenesulfonate A mechanically stirred suspension of 1,2-naphthoquinone (15.8 g, 0.1 mole), 1,4,5-trimethyl-1,2,4-triazolium-3-thiolate (15.7 g, 0.11 mole) and p-toluenesulfonic acid (38.0 g, 0.2 mole) in distilled water (200 ml) was maintained at ambient temperature (about 20° C.) in a nitrogen atsmphere for 18 hours. The deep red tarry material which separated initially was transformed to a red solid after the 18 hour period. The red solid was collected and washed with distilled water. This resulting salt was then dissolved in methanol and reprecipitated with ethyl ether. This reprecipitation procedure was repeated twice. The resulting light brown powder was suspended in ethanol with vigorous stirring. This procedure was repeated twice. The resulting ivory colored salt was washed with ethanol and then with ethyl ether to provide a yield of 19.8 g of the desired product (42% yield) having a melting point of 208°–209° C. (decomposed). The structure of the desired compound was confirmed by mass spectral analysis and by elemental analysis.

EXAMPLE 2

Preparation of
2-[1,4,5-trimethyl-1,2,4-triazolium-3-thio]-1,4-norbornanehydroquinone tetrafluoroborate A stirred methanol (100 ml) solution of norbornane-p-benzoquinone (10.4 g, 0.06 mole), 1,4,5-trimethyl-1,2,4-triazolium-3-thiolate (8.6 g, 0.06 mole) and 48% by weight tetrafluoroboric acid (10.5 g, 0.06 mole) was kept at ambient temperature (about 20° C.) for 18 hours. Most of the solvents were removed under reduced pressure. Methanol was added to the residual liquid from which a colorless solid separated. After standing at ambient temperature (about 20° C.) for about 30 minutes, the resulting salt was collected. The desired product had a melting point of 207°–209° C. and was identified by elemental analysis. The yield was 2.9 g (12%).

EXAMPLE 3

Photographic Material According to the Invention

The following compositions were prepared and coated at a 2-mil (50.8 microns) wet coating thickness on a gelatin-subbed poly(ethylene terephthalate) film support and heat-set for 5 minutes at 49° C.:

(a) Composition 3A:
0.24 micron AgCl, (0.66 kg Ag/mole): 0.7 g
Deionized photographic gelatin (10% by weight in water): 2.0 g
Distilled water: 2.0 g
Surfactant 10 G (10% by weight in water) (Surfactant 10 G is a p-isononylphenoxypolyglycidol, a trademark of and available from the Olin Corp., U.S.A.): 1 drop
1 normal nitric acid: 3 drops
Aqueous glutaraldehyde (10% by weight in water) (hardener): 2 drops (b) The silver chloride composition of (a) was prepared with the exception that the photographic gelatin, the surfactant, nitric acid and glutaraldehyde were replaced with 4 g of a 0.3 micron light fogged halide converted internally fogged silver chlorobromide gelatino emulsion (2.16 kg/mole). The internally fogged silver halide emulsion was prepared like that described in U.S. Pat. No. 2,592,250;

(c) The silver chloride composition as described in (b) was prepared with the exception that 8 mg of 4-[1,4,5-trimethyl-1,2,4-triazolium-3-thio]-1,2-naphthalenediol p-toluenesulfonate in 0.2 g of 2-methoxyethanol was added. This is a photographic composition of the invention.

Samples of each photographic element (a), (b) and (c) were imagewise exposed for $10^{-3}$ seconds in a commercial sensitometer to produce a developable latent image in each photographic element. Each photographic element was processed for 3 minutes in a commercially available developer solution like the following formulation:

Na$_2$SO$_3$: 72.0 g/liter
N-Methyl-p-aminophenol sulfate (developing agent): 5.0
Hydroquinone: 10.0
Sodium metaborate: 35.0
KBr: 5.0
NaOH or KOH: to pH 10.45 @ 22° C.

The developed photographic element was fixed for 10 minutes in Kodak F5 fixing bath (Kodak is a trademark of Eastman Kodak Company, U.S.A.) having the following composition:

Water (about 50° C.): 600 ml
Na$_2$S$_2$O$_3$.5H$_2$O: 240.0 g
Na$_2$SO$_3$: 15.0 g
28% acetic acid: 48 ml
Boric acid: 7.5 g
Potassium Alum.10H$_2$O: 15.0 g
Cold water to: 1.0 liter The fixed photographic elements were then washed for 5 minutes in water and dried. The photographic element (a) was a control. The photographic element (b) was a comparison photographic element. The relative speed, maximum density and gamma readings of the resulting images are given in the following Table I.

TABLE I

| Coating | gamma* | Diffuse D-max | Relative Speed** |
|---|---|---|---|
| a (control) | 1.3 | ~1.15 | 0 |
| b (comparison) | 1.6 | ~1.72 | 0 |
| c (invention) | 6.7 | ~2.96 | −0.3 log E |

*Approximate straight line slope, density units per log E.
**Measured at D = 0.1 above fog.

Comparison of photographic element (b) to photographic element (a) indicates that some halide solvent action occured; however, the incorporation of the naphthalenediol compound in coating (c) markedly enhanced maximum density even though a slight speed loss occurred. In photographic element (c) the 1,4,5-trimethyl-1,2,4-triazolium-3-thio silver ion complexing moiety was released imagewise because no internally fogged emulsion grains were developed in the unexposed areas.

EXAMPLE 4

1,2,4-Triazolium-3-thio Silver Ion Complexing Moiety With a Sulfur and Gold Sensitized Core-Shell Silver Halide Emulsion The following photographic compositions were prepared and coated on a gel-subbed poly(ethylene terephthalate) film support at a 2-mil (50.8 microns) wet coating thickness and heat-set for 5 minutes at 130° F. (55° C.):

(d)
5% deionized photographic gelatin containing 1 mg of Na$_2$EDTA: 2.0 g
Silver bromide (0.25 micron grain size) internally sulfur and gold sensitized core-shell gelatino emulsion (0.75 kg/mole): 2.0 g (no surface sensitization)
Silver bromide (1.5 micron grain size) tabular grain gelatino emulsion (0.91 kg/mole): 1.0 g
Surfactant (Surfactant 10 G, 10% by weight in water): 1 drop
0.5 Normal nitric acid: 5 drops
Ascorbic acid (antioxidant): 0.001 g
Glutaraldehyde (10% by weight in water) (hardener): 2 drops (e) The photographic composition in (d) was prepared but the composition also contained the following:
acetonitrile: 0.2 g
water: 1 drop
isopropylidene ascorbic acid: 0.001 g
4-[1,4,5-trimethyl-1,2,4-triazolium-3-thio]-1,2-naphthalenediol p-toluenesulfonate in 0.2 g of 2-methoxyethanol: 0.008 g Samples of each of photographic elements (d) and (e) were imagewise exposed for 10$^{-3}$ seconds in a commercial sensitometer to provide a developable latent image in each photographic element. The imagewise exposure was through a combination of Wratten 1A+36+38A filters (Wratten is a trademark of Eastman Kodak Company, U.S.A.) to provide a blue light exposure. The exposed photographic elements were then processed for 6 minutes in a developer composition like the following:

4-Hydroxymethyl-4-methyl-1-phenyl-3-pyrazolidone: 2.5 g
Chlorohydroquinone: 13.0
Na$_2$SO$_3$: 40.0
Sodium metaborate: 35.0
KBr: 5.0
NaOH: 3.5
Water: to one liter
pH adjusted to 10.4

The photographic elements were then fixed for 10 minutes in a Kodak F5 fixing bath as described in Example 3 and washed with water. A comparison of the photographic elements provided the following results:

TABLE II

| Coating | gamma* | Diffuse D-max | Relative Speed** |
|---|---|---|---|
| d (control) | 0.9 | 1.3 | 0 |
| e (invention) | 8.0 | >3.6 | +0.08 log E |

*Approximate straight line slope, density units per log E.
**Measured at D = 0.1 above fog.

Both photographic elements (d) and (e) provided negative images. In photographic element (e) the developing tabular grain silver halide caused oxidation of the thiolate releaser and release of the triazolium thiolate moiety. The released thiolate moiety etched away the shell of the internally imaged core-shell emulsion grains to reveal their internal image causing the larger gamma and maximum density increases that were observed.

In following Examples 5-8, other 1,2,4-triazolium-3-thio releasing compounds are illustrated.

EXAMPLE 5

The procedure described in Example 4 was repeated with the exception that the following compound replaced the naphthalenediol compound of Example 4: 4-[1,4,5-trimethyl-1,2,4-triazolium-3-thio]-1,2-naphthalenediol tetrafluoroborate. The resulting developed image had a maximum density of greater than 3.6 and a gamma of about 8.

EXAMPLE 6

The procedure described in Example 4 was repeated with the exception that the naphthalenediol compound was replaced by the following compound: 2-[1,4,5-trimethyl-1,2,4-triazolium-3-thio]-1,4-dihydroxy-5,6- dimethylbenzene tetrafluoroborate. The processed photographic element had a maximum density of greater than 3.6 and a gamma of about 6.

EXAMPLE 7

The procedure described in Example 4 was repeated with the exception that the naphthalenediol compound was replaced by 4-[1,4,5-trimethyl-1,2,4-triazolium-3-thio]-1,2-naphthalenediol trifluoroacetate. The processed photographic element had a maximum density of 3.2 and a gamma of about 6.

EXAMPLE 8

The procedure described in Example 4 was repeated with the exception that the naphthalenediol compound was replaced by the following compound: 2-[1,4,5-trimethyl-1,2,4-triazolium-3thio]-1,4-norbornanehydroquinone tetrafluoroborate. The processed photographic element had a maximum of density of greater than 2.8 and a gamma of about 5.

EXAMPLE 9

A photographic composition was prepared by mixing the following:
Silver bromide, cubic grain 0.25 micron grain size, core-shell gelatino emulsion having a fogged core (1.25 kg/mole): 1.5 g
Silver bromoiodide ($AgBr_{97.4}I_{2.6}$), 0.38 micron grain size, cubic grain, sulfur and gold chemically sensitized (1.19 kg/mole): 1.5 g
Deionized photographic gelatin (10% by weight in water): 2.0 g
Surfactant (Surfactant 10 G, 10% by weight in water): 1 drop
1 Normal sulfuric acid (to adjust pH to 5.0): 3 drops The resulting composition was melted and coated on a gel-subbed poly(ethylene terephthalate) film support at a 2-mil wet coating thickness (50.8 microns). The photographic coating was chill set to provide a control photographic element designated as j. A second coating, designated as photographic element k, was similarly prepared as photographic j with the exception that it additionally contained 6 mg of 2-[1,4,5-trimethyl-1,2,4-triazolium-3-thio]-1,4-norbornanehydroquinone tetrafluoroborate in 0.2 g of acetonitrile with 1 drop of distilled water.

A third photographic coating, designated as photographic element l, was similarly prepared as photographic element j with the exception that it additionally contained 3 mg of norbornane-p-hydroquinone.

Samples of each of photographic elements j, k and l were imagewise exposed to light through a 0.15 log E step tablet with a 1.0 neutral density filter for $10^{-2}$ seconds to provide a developable latent image in each photographic element. The exposure was by means of a light from a commercial sensitometer through Wratten filters 1A+36+38A to provide a blue light exposure. The exposed photographic elements were then processed for 5 minutes in a commercially available developer described in Example 3. After development, the resulting photographic elements were fixed for 10 minutes in Kodak F5 fixing bath, then washed for 5 minutes in water and finally dried. The maximum density, gamma and relative speed are summarized in following Table III.

TABLE III

| Coating | Relative Speed at Fog + 0.1 | gamma** | D-max |
|---|---|---|---|
| j (control) | 0 | 1.05 | 1.33 |
| k (invention) | −0.11 log E | 6.0 | 2.06 |
| l (comparison) | +0.10 log E | 1.35 | 1.37 |

**Approximate straight line slope, density units per log E.

Comparison of photographic elements j and l indicate that the incorporated developing agent provided a slight speed and gamma increase, but no significant increase in maximum density. Photographic element k (invention) provided a marked increase in gamma and maximum density with a slight loss in speed.

EXAMPLE 10

A photographic composition was prepared and adjusted to pH 5 with one normal sulfuric acid. A photographic coating (photographic element m) was then made by coating the composition on a gelatinsubbed poly(ethylene terephthalate) film support to provide the following coverages of the composition in $g/m^2$:
0.38 micron cubic grain sulfur and gold sensitized silver bromoiodide gelatino emulsion ($AgBr_{97.4}I_{2.6}$): 0.75 (as silver)
0.3 micron light fogged halide converted silver chlorobromide: 0.75 (as silver)
Gelatin (binder): 3.0
Surfactant (Triton X-200 which is sodium octylphenol poly(etheneoxy)sulfonate and is a trademark of Rohm & Haas Co., U.S.A.): 0.09
Bis[vinyl(sulfonylmethyl ether)] (hardener): 0.018
4-Hydroxy-5-bromo-6-methyl-1,3,3a,7-tetraazaindene (stabilizer): 0.007

A second photographic element, designated photographic element n, was prepared similarly to photographic element m with the exception that photographic element n contained 0.055 $g/m^2$ of 2-[1,4,5-trimethyl-1,2,4-triazolium-3-thio]-1,4-norbornanehydroquinone chloride.

Photographic elements m and n were imagewise exposed and processed as described in Example 9. The results are given in following Table IV.

TABLE IV

| Coating | Development time (min) | Relative Speed at fog +0.1 | gamma | D-max |
|---|---|---|---|---|
| m (control) | 3 | 0 | 1.15 | 1.22 |
| m (control) | 5 | +0.15 log E | 1.35 | 1.44 |
| n (invention) | 3 | +0.10 log E | 1.45 | 1.62 |
| n (invention) | 5 | +0.21 log E | 2.20 | 1.69 |

The photographic element n according to the invention is observed to provide high efficiency and uncovers the internal fog sites of the halide converted grains. This is illustrated as increased maximum density and gamma without loss in speed.

EXAMPLE 11

0.2 Micron cubic grain silver bromide gelatino emulsion grains were chemically fogged by means of dimethylamine borane. The emulsion grains were then provided with a shell of silver bromide to produce a grain size of about 0.25 microns. A melt was prepared and adjusted to pH 5 with one normal sulfuric acid. It was then coated to provide a photographic element o by coating on a gelatin-subbed poly(ethylene terephthalate) film support to provide the following coverages in g/m²:

- 0.38 micron cubic grain sulfur and gold sensitized silver bromoiodide (AgBr₉₇.₄I₂.₆): 0.85 (as silver)
- 0.25 micron core-shell silver bromide (fogged core): 0.85
- Gelatin: 3.4
- Surfactant (Triton X-200): 0.12
- Bis(vinylsulfonylmethyl ether) (hardener): 0.24
- 4-Hydroxy-5-bromo-6-methyl-1,3,3a,7-tetraazaindene (stabilizer): 0.09

A second photographic element, designated as photographic element p, was similarly prepared but additionally contained 0.037 g/m² of 2-[1,4,5-trimethyl-1,2,4-triazolium-3-thio]-1,4-dihydroxy-5,6-dimethylbenzene p-toluenesulfonate. An x-ray fluorescence analysis of photographic elements o and p showed that coverages in p were actually 12% higher than in o.

The photographic elements o and p were imagewise exposed and processed as described in Example 9. Results of the photographic elements are given in following Table V.

TABLE V

| Coating | Development time (min) | Relative Speed at fog +0.1 | gamma | D-max |
|---|---|---|---|---|
| o (control) | 3 | 0 | 0.9 | 0.92 |
| o (control) | 5 | +0.27 log E | 1.1 | 1.32 |
| p (invention) | 3 | +0.09 log E | 6.0 | 2.54 |
| p (invention) | 5 | +0.35 log E | 6.0 | 2.52 |

EXAMPLE 12

The procedure of Example 11 was repeated with the following changes:

The surface-sensitive emulsion was replaced with one comprising sulfur plus gold sensitized 0.8 micrometer AgBr cubic grains. The internally-fogged core/shell emulsion was comprised of grains having a 0.21 micrometer edge-length. The hardener was bis(vinylsulfonyl)methane. Coating q of following Table VI contained no redox releaser. Coating r additionally contained 0.03 g/meter² of

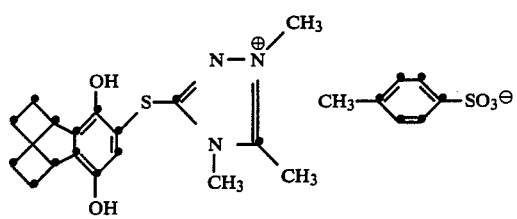

Coating s contained 0.036 g/meter² of the compound below as a replacement for the redox releaser in coating r.

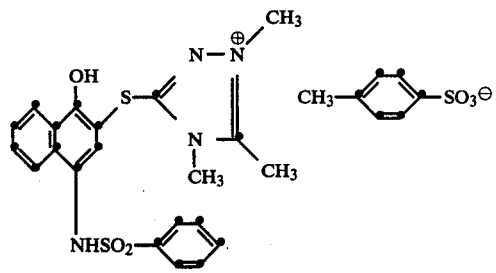

The exposure was reduced to 10⁻⁴ seconds and development was performed for 60 seconds at 35° C. (95° F.) rather than 5 minutes at room temperature (about 20° C.). Results are summarized in Table VI.

TABLE VI

| Coating | Relative Speed at fog +0.1 | Gamma* | D-max |
|---|---|---|---|
| q (control) | 0 | 3 | 2.6 |
| r (invention) | +0.05 log E | 7 | 2.6 |
| s (invention) | −0.15 log E | 7 | 2.75 |

*Approximate straight line slope, density units per log E.

EXAMPLE 13

An emulsion melt (A) was prepared as follows:

| Melt (A) | |
|---|---|
| 12.5% Aqueous deionized photographic gelatin | 8.0 g |
| Distilled water | 2.0 g |
| Surfactant 10G (10% by weight in water) (Surfactant 10G is a trademark of the Olin Company, U.S.A., and is a polyglycidol ether) | 3 drops |
| 1 Normal sulfuric acid | 6 drops |
| 0.8 micrometer cubic grain sulfur and gold sensitized silver bromoiodide gelatino emulsion (AgBr₉₇.₅I₂.₅, 0.83 kg/Ag mole) | 2.1 g |
| 0.3 micrometer cubic grain internally fogged AgBr core-shell gelatino emulsion (1.39 kg/Ag mole) | 3.0 g |

A redox-releaser Solution (B) was prepared containing 1 mg of ascorbic acid, 0.4 g of 2-methoxyethanol, and 8 mg of:

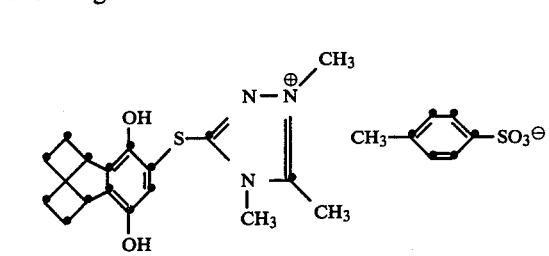

Another redox-releaser Solution (C) was prepared containing 1 mg of ascorbic acid, 0.4 g of 2-methoxyethanol, and 6 mg of

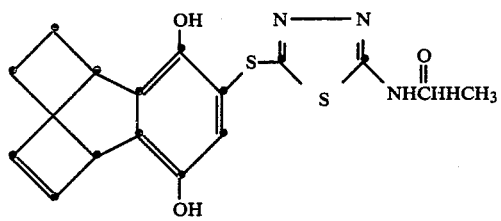

A coating melt t (control) was prepared by slowly adding 15 drops of 2-methoxyethanol to 5 g of stirred (A). The melt as then handcoated with a 100-micrometer doctor blade and chill-set.

A second coating melt u was prepared by slowly adding 15 drops of (B) to 5 g of stirred (A) and coating as above.

A third coating melt v was prepared by slowly adding 15 drops of (C) to 5 g of stirred (A) and coating as above.

Samples of each coating were exposed for $10^{-4}$ seconds in a commercially available sensitometer and then tray processed for 4 minutes at room temperature (about 20° C.) in the developing solution of Example 3. Results are summarized in following Table VII.

TABLE VII

| Coating | Relative Speed at fog +0.1 | Gamma* | D-max |
|---|---|---|---|
| t (control) | 0 | 0.4 | 0.9 |
| u (invention) | −0.13 | 1.1 | 1.8 |
| v (invention) | −0.3 | 1.4 | 1.9 |

*Approximate straight line slope, density units per log E.

EXAMPLE 14

A donor sheet was prepared by coating the following composition on a subbed poly(ethylene terephthalate) film support:

| | Coverage g/meter² |
|---|---|
| Sulfur and gold-sensitized cubic AgBr grains (0.8μ grain) | 1.0 |
| Deionized photographic gelatin | 2.0 |
| Redox releaser of element r | 0.077 |
| Bis(vinylsulfonyl)methane (hardener) | 0.026 |

A receiver sheet was prepared by coating the following composition on a subbed poly(ethylene terephthalate) film support:

| | Coverage g/meter² |
|---|---|
| 0.2 Micrometer cubic AgBr grains | 0.5 |
| NiS nuclei (development nuclei) | 6 × 10⁻⁵ |
| Deionized photographic gelatin | 2.0 |
| Poly(2-methyl-4-vinyl-N—methyl pyridinium methylsulfate) (mordant) | 0.01 |

Both donor and receiver sheets were overcoated with 0.5 g/m² of gelatin containing 0.007 g/m² of bis(vinylsulfonyl) methane. A sample of the donor sheet was exposed as in Example 13.

A viscous developing solution was prepared by thickening a commercially available developer to give the following composition:

(Ethylenedinitrilo)tetraacetic acid, tetrasodium salt: 5 g
Sodium sulfite: 65 g
Sodium bromide: 4.3 g
N-Methyl-p-aminophenol sulfate (developing agent): 10 g
Potassium hydroxide: 59 g
Hydroquinone: 40 g
Carboxymethyl cellulose: 5.5 g
Water to make 1 liter of solution The viscous developer was applied to the exposed donor sheet with a 150-micrometer doctor blade. The receiver sheet was immediately laminated to the exposed donor sheet. After 3 minutes, the sheets were peeled apart, development stopped in a stop bath, fixed, washed and dried. Following Table VIII summarizes the results.

TABLE VIII

| Coating | Relative Speed at fog +0.1 | Gamma* | D-max/D-min |
|---|---|---|---|
| Donor | 0 | 1.1 | 0.8/0.06 |
| Receiver | 0.5 | 3 | 1.6/0.26 |

*Approximate straight line slope, density units per log E.

This example demonstrates the use of imagewise-released silver ion complexing moieties to cause physical development onto catalytic nuclei thereby producing high covering power negative images.

EXAMPLE 15

A coating melt was prepared according to the following composition:

0.3 Micrometer internally fogged cubic AgBr core/shell gelatino emulsion (1.24 kg/Ag mole): 1 g
0.2 Micrometer cubic AgBr gelatino emulsion (0.84 kg/mole): 1 g
Deionized photographic gelatin (10% by weight in water): 3 g
Surfactant 10G (10% by weight in water): 1 drop
1 Normal sulfuric acid (to adjust final melt pH to 5): 3 drops Coating w (control) was then prepared by adding a solution containing 0.2 g acetonitrile, 1 drop distilled water, and 1 mg of ascorbic acid to the above melt composition, thoroughly mixing, and then handcoating (with chill-setting) the melt with a 50-micrometer doctor blade onto a subbed poly(ethylene terephthalate) film support.

Coating x was prepared the same as coating w with the solution additionally containing 7 mg of

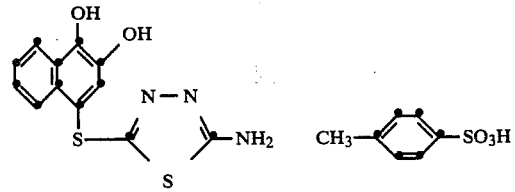

Coating y was prepared the same as coating w with the solution additionally containing 7 mg of

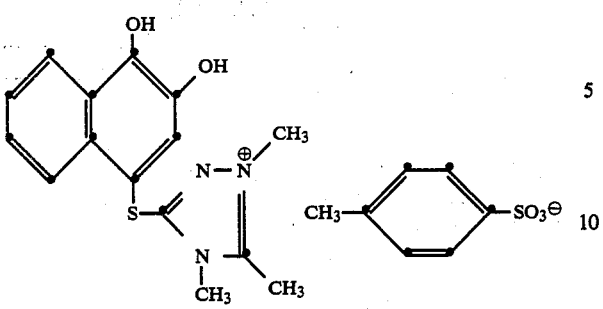
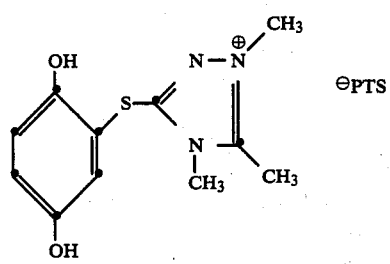

Samples of each coating were then exposed $10^{-2}$ seconds through an 0.15 log E step tablet and Wratten filters 1A+36+38A. Wratten is a trademark of Eastman Kodak Company, U.S.A. Each was then developed for 5 minutes in the developer of Example 16, fixed in the composition below, washed 5 minutes in water and dried.

Sodium thiosulfate pentahydrate: 240.0 g
Sodium sulfite: 15.0 g
Acetic acid (28% by weight): 48 mls
Boric acid: 7.5 g
Potassium alum dodecahydrate: 15.0 g
Water to make one liter of solution Results are summarized in following Table IX.

TABLE IX

| Coating | Relative speed at fog +0.1 | Gamma* | D-max |
|---|---|---|---|
| w (control) | 0 | 1.65 | 1.3 |
| x (invention) | −0.5 | ~7 | 1.9 |
| y (invention) | 0 | ~6 | 1.6 |

*Approximate straight line slope, density units per log E.

EXAMPLE 16

The following compositions were prepared and coated at a wet laydown of 0.63 ml/dm² on a gelatin-subbed poly(ethylene terephthalate) film support and then gelatin overcoated at a wet laydown of 0.35 ml/dm².

(z1) Seventeen grams of a 0.65 micron AgBr$_{98}$I$_2$ emulsion (0.813 kg/Ag mole) and 41.25 grams of a 0.25 micron internally-fogged core-shell emulsion (0.75 moles shell/1.0 moles core, 1.019 kg/Ag mole) were mixed with 33.54 grams of 20% aqueous gelatin and 44.2 grams of distilled water. The mixture was warmed to 40° C. and the following additions made: 1.1 ml of 1 Normal sulfuric acid, 6.6 ml of 6.7% by weight aqueous bis(vinylsulfonyl) methane, 3.0 ml of a solution containing 5.0 g of the sodium salt of 4-hydroxy-6-methyl-1,3,3a,7-tetraazaindene in 100 ml of distilled water, and 3.7 ml of a solution containing 3.4 ml of 2 Normal propionic acid and 6.8 g of p-tertiary-octylphenoxyethoxyethylsulfonate (sodium salt) in 100 ml of distilled water.

(z2) Composition z2 was prepared the same as z1 but additionally containing 223 mg of the redox releaser below dissolved in 5 milliliters of tetrahydrofuran and 3 ml of distilled water.

(z3) Composition z3 was prepared the same as z2 but additionally containing another 223 mg of the same redox releaser.

Samples of each coating were exposed through a filter package containing a Wratten 36 and 38A and 0.5 neutral density filter for $10^{-4}$ second in a commercial sensitometer (EG&G) to produce a developable latent image. Each sample was then processed in a RECORDAK PROSTAR ™ FILM PROCESSOR, Model DVR, manufactured by the Eastman Kodak Company. RECORDAK and PROSTAR are trademarks of Eastman Kodak Company, U.S.A. Development time was 45 seconds at 95° F. (35° C.) in a developing solution like the following:

N-methyl-p-aminophenol sulfate (developing agent): 5.0 g/liter
Hydroquinone: 10.0 g/liter
Sodium sulfite: 72.0 g/liter
Sodium metaborate: 35.0 g/liter
Sodium hydroxide: 3.5 g/liter
Potassium bromide: 5.0 g/liter
Water to make: 1.0 liter The developed samples were then fixed for 45 seconds in a hardening-fix composition, like the following:

| Component | Amount |
|---|---|
| Water, about 50° C. (125° F.) | 600 milliliters |
| Sodium Thiosulfate (Pentahydrated) | 360.0 grams |
| Ammonium Chloride | 50.0 grams |
| Sodium Sulfite (Anhydrous) | 15.0 grams |
| 28% Acetic Acid* | 48.0 milliliters |
| Boric Acid, Crystals** | 7.5 grams |
| Potassium Alum, Fine Granular (Dodecahydrated) | 15.0 grams |
| Cold water to make | 1.0 liter |

*To make approximately 28% acetic acid from glacial acetic acid, add 3 parts of glacial acetic acid to 8 parts of water.
**Use crystalline boric acid as specified. Powdered boric acid dissolves only with great difficulty and its use should be avoided.

Each sample was then washed and dried and measurements made. The maximum and minimum densities (neutral diffuse) and gamma readings are given in the following Table X.

TABLE X

| Coating | D-max/D-min | Gamma* |
|---|---|---|
| z1 (control) | 1.43/0.05 | 1.15 |
| z2 (invention) | 3.63/0.07 | 4.2 |
| z3 (invention) | 4.06/0.09 | 7.0 |

*Approximate straight line slope, density units per log E.

EXAMPLE 17

Control Coating (Z4)

Composition

Deionized photographic gelatin: 8.1 g
Distilled water: 88.5 ml
6.8% by weight aqueous solution of TRITON X-100 (p-tert-octylphenoxy ethoxy ethyl sulfonate, sodium salt): 4.0 ml
Normal sulfuric acid: 1.4 ml
1 Normal potassium bromide: 1.3 ml
0.23 Micron AgBr, internally fogged cubic grains gelatino emulsion (0.922 Kg/Ag mole): 21.4 g
0.85 Micron AgBr, internally sulfur and gold sensitized, surface sulfur sensitized gelatino emulsion (0.889 Kg/Ag mole): 20.6 g To the above composition was added 5 ml of a methanol solution containing 0.010 g of ascorbic acid and 0.002 g of

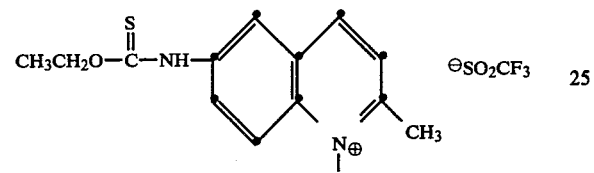

Five milliliters of an aqueous hardener solution was added just before coating consisting of 2% bis(vinyl-sulfonylmethyl) ether.

Invention Coating (Z5)

Composition

Preparation of the control was repeated, except that the 5 ml of methanol solution also contained 100 mg of

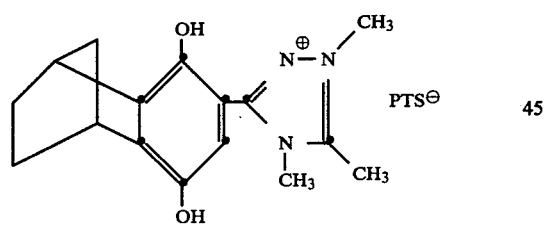

Both control and invention compositions were coated onto gelatin-subbed polyethylene terephthalate film support at a wet laydown of 6 ml/ft² (0.65 ml/dm²) to give an aim silver coverage of 2 g/m².

Samples of each coating were exposed for $10^{-2}$ seconds in a commercial sensitometer through a step tablet plus 0.75 neutral density, Wratten 1A plus 36 and 38A filters. Test samples were processed in a developer similar to that of Example 14 except that carboxymethyl cellulose was omitted and 150 mg/liter of 5-methylbenzotriazole were added. Optimal processing times at 95° F. (36.5° C.) were 40 seconds for the control and 45 seconds for the invention. A comparison of sensitometric properties is shown in the following Table XI.

TABLE XI

| Coating | Gamma* | D-max | Relative Speed (log E) |
|---|---|---|---|
| Z-4 (Control) | 4.0 | 1.92 | 0 |
| Z-5 (Invention) | 5.5 | 2.09 | +0.1 |

*Approximate straight line slope; density units per log E.

The redox release carrier compounds given in following Examples 18-38 were prepared by procedures like those described in Examples 1 and 2 (the number in parenthesis is the melting point):

EXAMPLE 18

(mp=208°–209° C.).

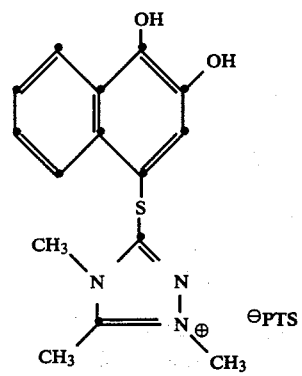

EXAMPLE 19

(mp=167°–169° C.).

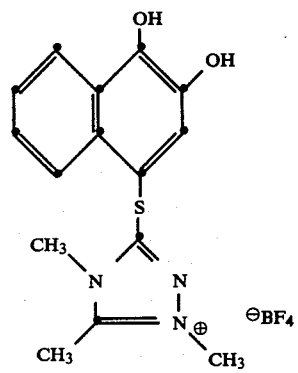

EXAMPLE 20

(mp=155°–157° C.).

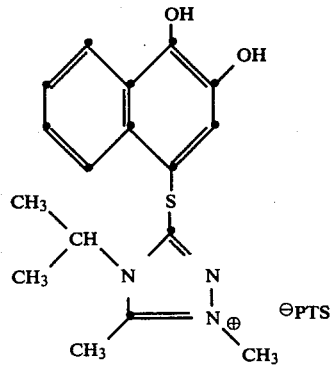

EXAMPLE 21
(mp=175°-177° C.).
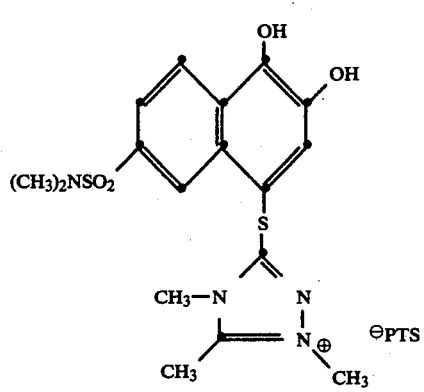
EXAMPLE 22
(mp=180°-181° C.).
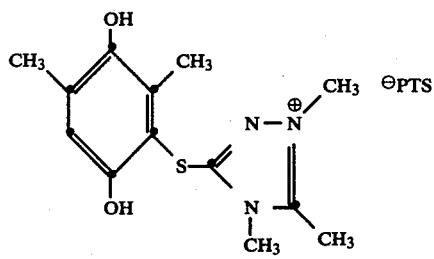
EXAMPLE 23
(mp—229°-330° C.).
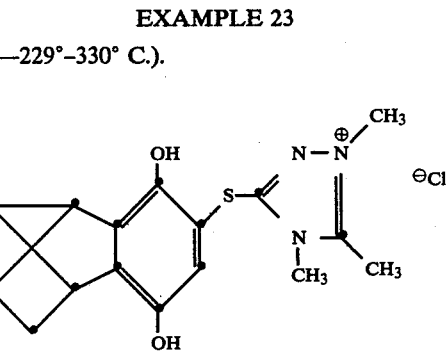
EXAMPLE 24
(A) (⊖BF$_4$ salt mp=97°-98° C.).
(B) (⊖Cl salt mp=248° C.).
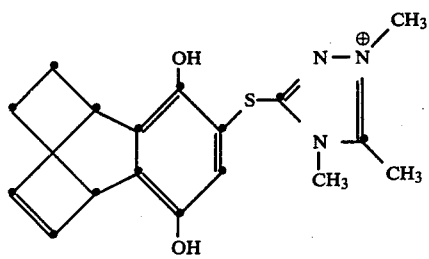
EXAMPLE 25
(A) (⊖PTS salt mp=194°-195° C.).
(B) (⊖CF$_3$CO$_2$ salt mp=214°-215° C.).
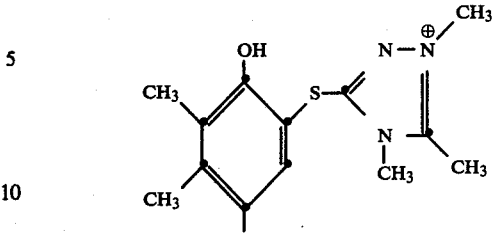
EXAMPLE 26
(mp=214°-215° C.).
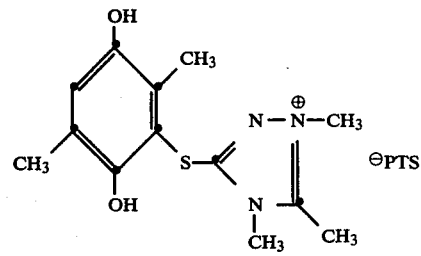
EXAMPLE 27
(A) (⊖BF$_4$ salt mp=162° C.).
(B) (⊖PTS salt mp=194°-195° C.).
(C) (⊖CF$_3$CO$_2$ salt mp=137°-138° C.).
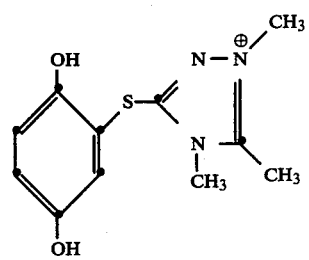
EXAMPLE 28
(mp=220°-222° C.).
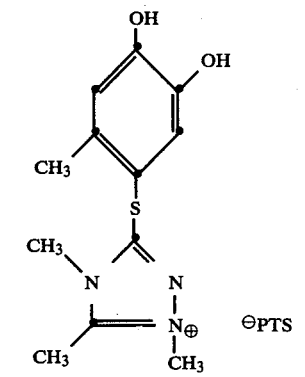
EXAMPLE 29
(A) (⊖PTS salt mp=250°-251° C.).
(B) (⊖BF$_4$ salt mp=197°-198° C.).

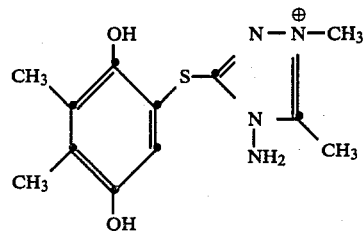
EXAMPLE 30
(mp=196° C.).
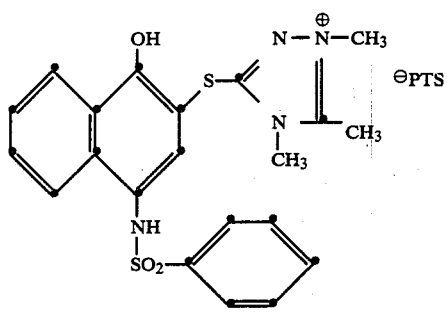
EXAMPLE 31
(mp=182°–183° C.).
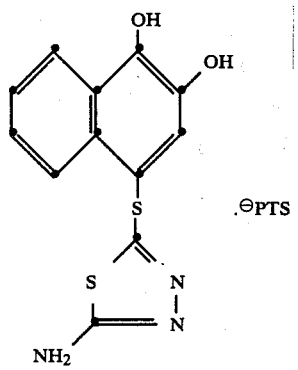
EXAMPLE 32
(mp=252° C. dec.).
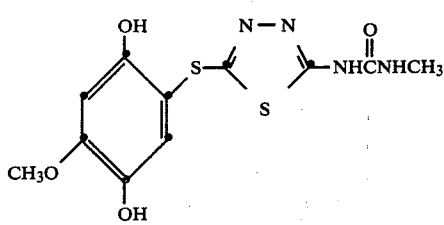
EXAMPLE 33
(mp=255° C.).
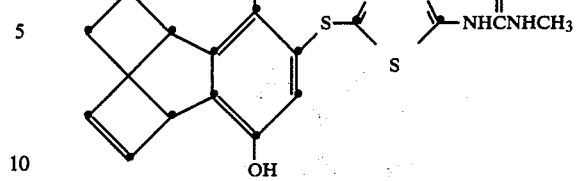
EXAMPLE 34
(mp=238° C.).
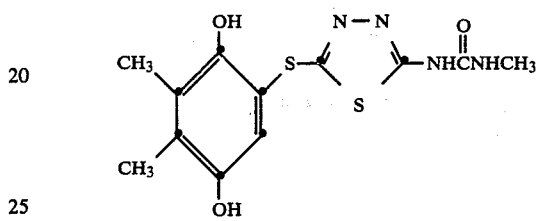
EXAMPLE 35
(mp=104° C.).
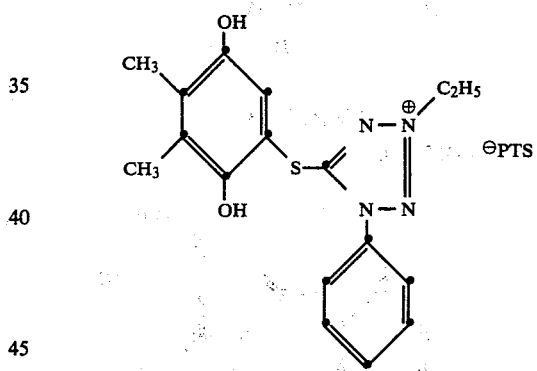
EXAMPLE 36
(mp=281° C. dec.).
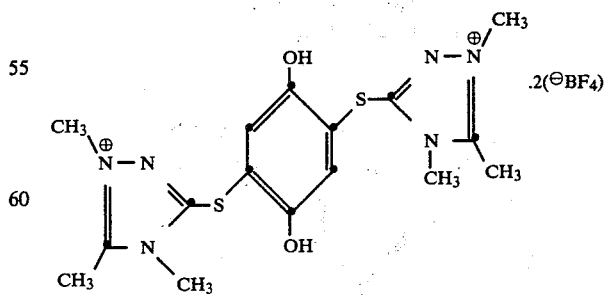
EXAMPLE 37
(mp=94°–96° C.).

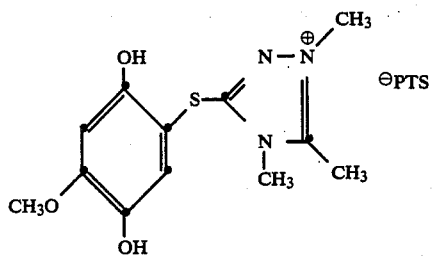

EXAMPLE 38

(mp=214° C.).

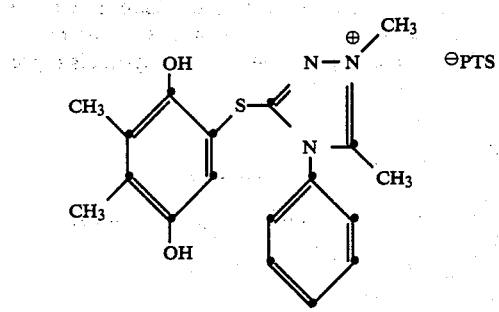

The invention has been described in detail with particular reference to preferred embodiments thereof, but it will be understood that variations and modifications can be effected within the spirit and scope of the invention.

What is claimed is:

1. In a photographic element comprising a support bearing a combination of
   (i) photographic silver halide capable of forming a surface latent image, and
   (ii) a photographic silver halide capable of forming an internal latent image;

the improvement wherein there is present in reactive association with said surface latent image silver halide, a redox release carrier compound containing a silver ion complexing heterocyclic thio moiety that is capable of being released upon oxidation of said redox release carrier compound, as a function of development of said surface latent image silver halide and migrating to the internal latent image silver halide to uncover the internal latent image and rendering the internal latent image silver halide developable.

2. A photographic element as in claim 1 wherein said photographic silver halide capable of forming an internal latent image is a covered grain photographic silver halide having lower photosensitivity than said silver halide capable of forming a surface latent image.

3. A photographic element as in claim 1 wherein said redox release carrier compound comprises a silver ion complexing 1,2,4-triazolium-3-thio moiety that is capable of being released upon oxidation of said redox release carrier.

4. A photographic element as in claim 1 wherein said redox release carrier compound is represented by the formula:

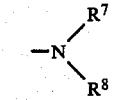

wherein:
R is a redox release carrier moiety capable upon oxidation of releasing a silver ion complexing moiety;
$R^1$, $R^2$ and $R^3$ are individually alkyl containing 1 to 25 carbon atoms, alkenyl containing 2 to 25 carbon atoms, aryl containing 6 to 25 carbon atoms, alkoxy containing 1 to 25 carbon atoms or $$-N\begin{matrix}R^7\\R^8\end{matrix};$$

$R^7$ is hydrogen or alkyl containing 1 to 25 carbon atoms;
$R^8$ is hydrogen, alkyl containing 1 to 25 carbon atoms or aryl containing 6 to 25 carbon atoms;
X is an anion.

5. A photographic element as in claim 1 wherein said redox release carrier compound is a phenolic silver halide developing agent.

6. A photographic element as in claim 1 wherein said redox release carrier compound is a phenolic silver halide developing agent represented by the formula:

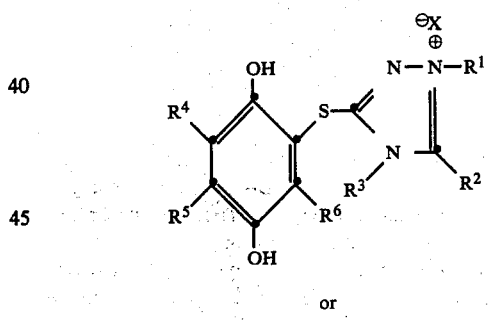

or

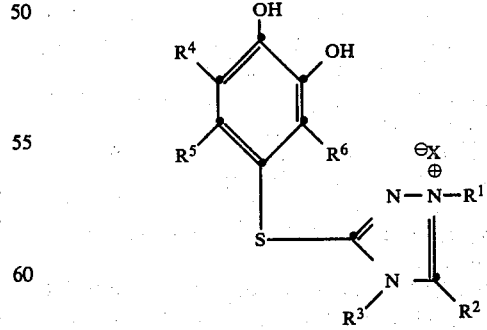

wherein:
$R^1$, $R^2$ and $R^3$ are individually alkyl containing 1 to 25 carbon atoms, alkenyl containing 2 to 25 carbon atoms, aryl containing 6 to 25 carbon atoms, alkoxy containing 1 to 25 carbon atoms or

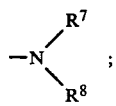

$R^4$, $R^5$ and $R^6$ are individually hydrogen; alkyl containing 1 to 25 carbon atoms; alkoxy containing 1 to 25 carbon atoms; sulfamyl; halo; or $R^4$ and $R^5$ together are the atoms necessary to complete a (i) carbocyclic or (ii) 5 or 6 member heterocyclic ring;

$R^7$ is hydrogen or alkyl containing 1 to 25 carbon atoms;

$R^8$ is hydrogen, alkyl containing 1 to 25 carbon atoms or aryl containing 6 to 25 carbon atoms; and, X is an anion.

7. A photographic element as in claim 1 wherein said redox release carrier compound is a silver halide developing agent represented by the formula:

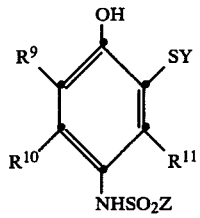

or

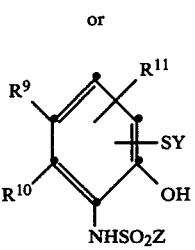

wherein:

Y is a silver ion complexing moiety capable of being released upon oxidation of the phenolic moiety;

Z is alkyl containing 1 to 25 carbon atoms or aryl containing 6 to 25 carbon atoms;

$R^9$, $R^{10}$ and $R^{11}$ are individually hydrogen, alkyl containing 1 to 25 carbon atoms, alkoxy containing 1 to 25 carbon atoms, sulfamyl or halo; or $R^9$ and $R^{10}$ taken together are the atoms necessary to complete a carbocyclic ring or a heterocyclic ring.

8. A photographic element as in claim 1 wherin said redox release carrier compound is a compound selected from the group consisting of
 (a) 4-[1,4,5-trimethyl-1,2,4-triazolium-3-thio]-1,2-naphthalenediol p-toluenesulfonate;
 (b) 2-[1,4,5-trimethyl-1,2,4-triazolium-3-thio]-1,4-hydroxy-5,8-ethano-5,8-dihydronaphthalene p-toluenesulfonate;
 (c) 2-[1,4,5-trimethyl-1,2,4-triazolium-3-thio]-1,4-dihydroxy-5,6-dimethylbenzene tetrafluoroborate;
 (d) 2-[1,4,5-trimethyl-1,2,4-triazolium-3-thio]-1,4-dihydroxy-5,8-ethano-5,6,7,8-tetrahydronaphthalene p-toluenesulfonate; and,
 (e) 2-[1,4,5-trimethyl-1,2,4-triazolium-3-thio]-1,4-norbornanehydroquinone tetrafluoroborate, and combinations thereof.

9. A photographic element as in claim 1 wherin said redox release carrier compound is represented by the formula:

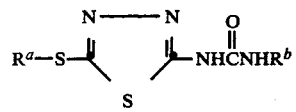

wherein:

$R^a$ is a redox release carrier moiety capable upon oxidation of releasing a silver ion complexing moiety;

$R^b$ is alkyl containing 1 to 25 carbon atoms or aryl containing 6 to 12 carbon atoms.

10. A photographic element as in claim 1 wherein said redox release carrier compound is a compound selected from the group consisting of compounds represented by the formulas:

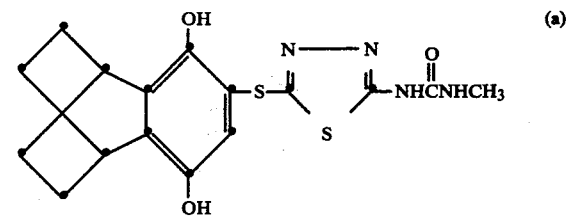

(a)

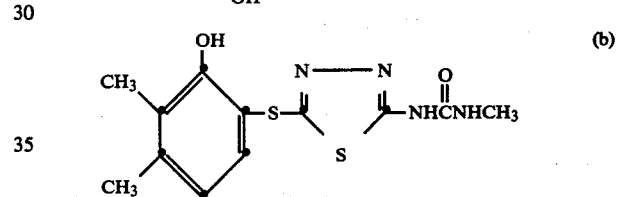

(b)

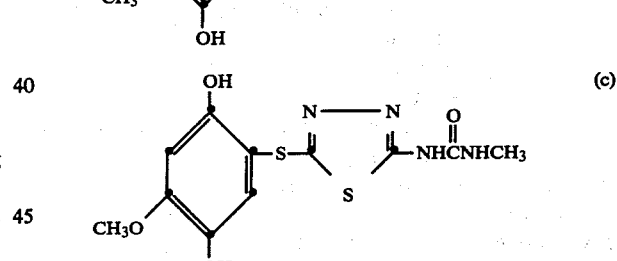

(c)

and

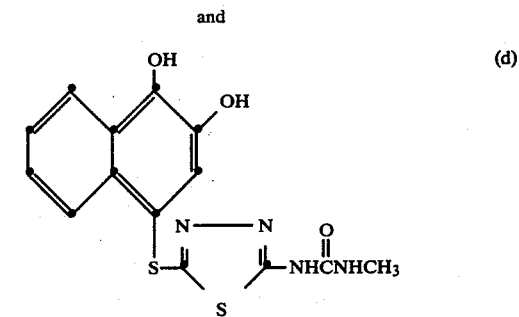

(d)

and combinations thereof.

11. In a photographic element comprising a support bearing,
 (a) photographic silver halide, and
 (b) a redox release carrier compound containing a silver ion complexing heterocyclic thio moiety that is capable of being released upon oxidation of said redox release carrier, the improvement wherein, said silver ion complexing heterocyclic thio moiety is a 1,2,4-triazolium-3-thio moiety.

12. A photographic element as in claim 11 wherein said redox release carrier compound is represented by the formula:

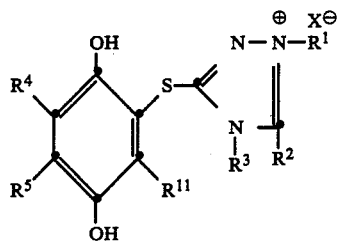

or

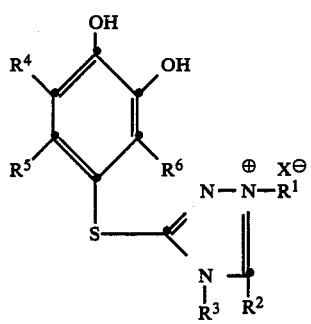

wherein:

R$^1$, R$^2$ and R$^3$ are individually alkyl containing 1 to 25 carbon atoms, alkenyl containing 2 to 25 carbon atoms, aryl containing 6 to 25 carbon atoms, alkoxy containing 1 to 25 carbon atoms or

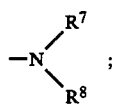

R$^4$, R$^5$ and R$^6$ are individually hydrogen, alkyl containing 1 to 25 carbon atoms, alkoxy containing 1 to 25 carbon atoms, sulfamyl, halo, or R$^4$ and R$^5$ together are the atoms necessary to complete a (i) carbocyclic ring or (ii) 5 or 6 member heterocyclic ring;

R$^7$ is hydrogen or alkyl containing 1 to 25 carbon atoms;

R$^8$ is hydrogen, alkyl containing 1 to 25 carbon atoms or aryl containing 6 to 25 carbon atoms;

X is an anion.

13. A photographic element as in claim 11 wherein said redox release carrier compound is represented by the formula:

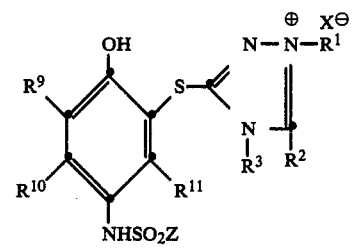

or

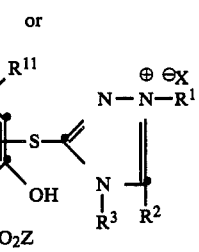

wherein:

R$^1$, R$^2$ and R$^3$ are individually alkyl containing 1 to 25 carbon atoms, alkenyl containing 2 to 25 carbon atoms, aryl containing 6 to 25 carbon atoms, alkoxy containing 1 to 25 carbon atoms or

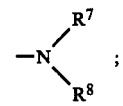

Z is alkyl containing 1 to 25 carbon atoms or aryl containing 6 to 25 carbon atoms;

R$^9$, R$^{10}$ and R$^{11}$ are individually hydrogen, alkyl containing 1 to 25 carbon atoms, alkoxy containing 1 to 25 carbon atoms, sulfamyl or halo; or R$^9$ and R$^{10}$ taken together are the atoms necessary to complete a carbocyclic ring or a heterocyclic ring;

X is an anion.

14. A photographic element as in claim 11 wherein said redox release carrier compound is a compound selected from the group consisting of:

(a) 4-[1,4,5-trimethyl-1,2,4-triazolium-3-thio]-1,2-naphthalenediol p-toluenesulfonate;

(b) 2-[1,4,5-trimethyl-1,2,4-triazolium-3-thio]-1,4-hydroxy-5,8-ethano-5,8-dihydronaphthalene p-toluenesulfonate;

(c) 2-[1,4,5-trimethyl-1,2,4-triazolium-3-thio]-1,4-dihydroxy-5,6-dimethylbenzene tetrafluoroborate;

(d) 2-[1,4,5-trimethyl-1,2,4-triazolium-3-thio]-1,4-dihydroxy-5,8-ethano-5,6,7,8-tetrahydronaphthalene p-toluenesulfonate; and, (e) 2-[1,4,5-trimethyl-1,2,4-triazolium-3-thio]-1,4-norbornanehydroquinone tetrafluoroborate, and combinations thereof.

15. A photographic silver halide element as in claim 11 comprising a binder.

16. A method of forming an image in an exposed photographic silver halide element as defined in claim 1 comprising developing said element by means of a surface type silver halide developer.

17. A method of forming an image in an exposed photographic silver halide element as defined in claim 5 comprising developing said element by means of a surface type silver halide developer.

* * * * *